United States Patent
Khosla et al.

(10) Patent No.: US 6,984,515 B2
(45) Date of Patent: Jan. 10, 2006

(54) MACROLIDE ANALOGS

(75) Inventors: Chaitan Khosla, Palo Alto, CA (US); Gary Ashley, Alameda, CA (US); Camilla Kao, Palo Alto, CA (US); Robert McDaniel, Palo Alto, CA (US)

(73) Assignees: The LeLand Stanford Junior University, Palo Alto, CA (US); Kosan Biosciences, Inc., Hayward, CA (US)

(*) Notice: Subject to any disclaimer, the term of this patent is extended or adjusted under 35 U.S.C. 154(b) by 363 days.

(21) Appl. No.: 09/852,416

(22) Filed: May 9, 2001

(65) Prior Publication Data

US 2003/0040084 A1 Feb. 27, 2003

Related U.S. Application Data

(63) Continuation of application No. 09/073,538, filed on May 6, 1998, now Pat. No. 6,558,942, which is a continuation-in-part of application No. 08/846,247, filed on Apr. 30, 1997, now Pat. No. 6,391,594, which is a continuation-in-part of application No. 08/486,645, filed on Jun. 7, 1995, now Pat. No. 5,712,146, which is a continuation-in-part of application No. 08/238,811, filed on May 6, 1994, now Pat. No. 5,672,491, which is a continuation-in-part of application No. 08/164,301, filed on Dec. 8, 1993, now abandoned, which is a continuation of application No. 08/123,732, filed on Sep. 20, 1993, now abandoned.

(51) Int. Cl.
*C12Q 1/00* (2006.01)
*C12P 1/00* (2006.01)

(52) U.S. Cl. .................. 435/253.5; 435/41; 435/76; 435/4; 435/183; 514/29; 536/7.1

(58) Field of Classification Search ............ 435/132, 435/183, 435, 91.4, 76, 252.35, 320.1, 253.5; 536/7.1; 514/29
See application file for complete search history.

(56) References Cited

U.S. PATENT DOCUMENTS

| | | | |
|---|---|---|---|
| 5,672,491 A | 9/1997 | Khosla et al. | 435/148 |
| 5,712,146 A | 1/1998 | Khosla et al. | 435/252.35 |
| 5,824,513 A | 10/1998 | Katz et al. | 435/76 |
| 5,876,991 A | 3/1999 | DeHoff et al. | 435/183 |
| 5,945,320 A | 8/1999 | Burgett et al. | 435/183 |
| 5,962,290 A | 10/1999 | Khosla et al. | 435/183 |
| 6,004,787 A | 12/1999 | Katz et al. | 435/183 |
| 6,033,883 A * | 3/2000 | Barr et al. | 435/148 |
| 6,060,234 A | 5/2000 | Katz et al. | 435/4 |
| 6,063,561 A | 5/2000 | Katz et al. | 435/4 |
| 6,066,721 A | 5/2000 | Khosla et al. | 536/23.1 |
| 6,080,555 A | 6/2000 | Khosla et al. | 435/41 |
| 6,200,813 B1 | 3/2001 | Katz et al. | 435/477 |
| 6,271,255 B1 | 8/2001 | Leadlay et al. | 514/450 |
| 6,391,594 B1 | 5/2002 | Khosla et al. | 435/91.4 |
| 6,399,789 B1 | 6/2002 | Santi et al. | 549/271 |
| 6,403,775 B1 | 6/2002 | McDaniel | 536/7.2 |
| 6,500,960 B1 | 12/2002 | Khosla et al. | 549/264 |
| 6,558,942 B1 | 5/2003 | Khosla et al. | 435/253.5 |
| 2002/0192756 A1 | 12/2002 | Santi et al. | 435/69.1 |
| 2003/0124680 A1 | 7/2003 | Reeves et al. | 435/76 |

FOREIGN PATENT DOCUMENTS

| | | |
|---|---|---|
| WO | WO 98/01546 | 1/1998 |
| WO | WO 98/01571 | 1/1998 |

OTHER PUBLICATIONS

Kuhstoss et al., Gene (1996) 183:231–236.
Oliynyk et al., Chem. and Biol. (1996) 3:833–839.
Reeves, C.D., et al., *Biochemistry*, 40:15464–15470 (2001).
McDaniel, R., et al., *Proc. Natl. Acad. Sci. USA*, 96:1846–1851 (1999).

* cited by examiner

*Primary Examiner*—Padmashri Ponnaluri
(74) *Attorney, Agent, or Firm*—Morrison & Foerster LLP

(57) ABSTRACT

A polyketide or glycosylated polyketide which has the formula:

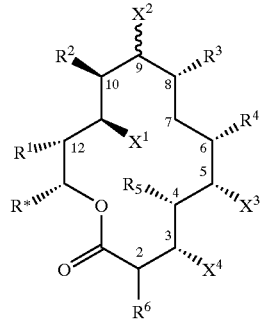

wherein R* is methyl or ethyl;
each of $R^1$-$R^6$ is methyl;
$X^1$ is OH or H; and/or
$X^2$ is =O, OH or H;
$X^3$ is OH or H;
$X^4$ is OH or H;
a pi bond is present at positions 10-11, 8-9, 4-5 and/or 2-3; and wherein at least one of the following characteristics is present:
$X^1$ is H;
$X^2$ is OH or H;
$X^3$ is H;
$X^4$ is H; or
a pi bond is present at positions 10-11, 8-9, 4-5 and/or 2-3.

7 Claims, 22 Drawing Sheets

Post-PKS Biosynthesis of Erythromycins

104

105

X=F, Cl, Br, $N_3$, OH, O-alkyl, S-alkyl, CN, O-acyl, O-aryl, $NH_2$, NH-alkyl, $N(alkyl)_2$

106

X= F; Y=H, Br, I, OH, O-alkyl, O-aryl, $N_3$, CN, S-alkyl, S-aryl
X= OH, Y=OH
X,Y= -O-, -NH-, -NR- 107
X=F, Cl, Br

108: X=H
109: X=OH

110

X=O-alkyl, O-aryl, $NH_2$, NH-alkyl, N-$(alkyl)_2$, NH-aryl 111
(R=H, alkyl, aryl)

112
(R=H, alkyl, aryl)

10-deoxymethynolide
210 methynolide
211 methymycin
212 neomethymycin
213

201

202

203

204

10-epi-methynolide
205

206

207

208

209

MACROLIDE ANALOGS

CROSS-REFERENCE TO RELATED APPLICATIONS

This application is a continuation of U.S. Ser. No. 09/073,538, filed 6 May 1998, now U.S. Pat. No. 6,558,942, which is a continuation-in-part of U.S. Ser. No. 08/846,247, filed 30 Apr. 1997, now U.S. Pat. No. 6,391,594, which is a continuation-in-part of U.S. Ser. No. 08/486,645, filed 7 Jun. 1995, now U.S. Pat. No. 5,712,146, which is continuation-in-part of U.S. Ser. No. 08/238,811, filed 6 May 1994, now U.S. Pat. No. 5,672,491, which is a continuation-in-part of U.S. Ser. No. 08/164,301, filed 8 Dec. 1993, now abandoned, which is a continuation-in-part of U.S. Ser. No. 08/123,732, filed 20 Sep. 1993, now abandoned. Priority is claimed under 35 USC §120. The disclosures of these applications are incorporated herein by reference.

REFERENCE TO GOVERNMENT FUNDING

This work was supported in part by a grant from the National Institutes of Health, CA66736. The U.S. government has certain rights in this invention.

TECHNICAL FIELD

The invention relates to the field of combinatorial libraries, to novel polyketides and antibiotics and to methods to prepare them. More particularly, it concerns construction of new polyketides and to libraries of polyketides synthesized by polyketide synthases derived from a naturally occurring PKS, as illustrated by the erythromycin gene cluster.

BACKGROUND ART

Polyketides represent a large family of diverse compounds ultimately synthesized from 2-carbon units through a series of Claisen-type condensations and subsequent modifications. Members of this group include antibiotics such as tetracyclines, anticancer agents such as daunomycin, and immunosuppressants such as FK506 and rapamycin. Polyketides occur in many types of organisms including fungi and mycelial bacteria, in particular, the actinomycetes.

A number of lactones of keto acids have been synthesized using standard organic chemistry. These include a series of unsaturated ketolactones synthesized by Vedejes et al., *J. Am Chem Soc* (1987) 109:5437–5446, shown as formulas 201, 202 and 203 in FIG. 11 herein. Additional compounds of formulas 204 and 205, also shown in FIG. 11 were synthesized as reported by Vedejes et al. *J Am Chem Soc* (1989) 111:8430–8438. In addition, compounds 206–208 (FIG. 11) were synthesized by Borowitz, (1975) Mass spectra of 6-ketononanolides and related ketolactones, *J. Heterocyclic Chem.* 12(1):101–106; compound 209 has been synthesized by Ireland et al., *J Org Chem* (1980) 45:1868–1880.

The polyketides are synthesized in vivo by polyketide synthases (PKS). This group of enzymatically active proteins is considered in a different category from the fatty acid synthases which also catalyze condensation of 2-carbon units to result in, for example, fatty acids and prostaglandins. Two major types of PKS are known which are vastly different in their construction and mode of synthesis. These are commonly referred to as Type I or "modular" and Type II, "aromatic."

The PKS scaffold that is the subject of the present invention is a member of the group designated Type I or "modular" PKS. In this type, a set of separate active sites exists for each step of carbon chain assembly and modification, but the individual proteins contain a multiplicity of such separate active sites. There may be only one multifunctional protein of this type, such as that required for the biosynthesis of 6-methyl salicylic acid (Beck, J. et al., *Eur J. Biochem* (1990) 192:487–498; Davis, R. et al., *Abstracts of Genetics of Industrial Microorganism Meeting, Montreal, Abstract P288* (1994)). More commonly, and in bacterial-derived Type I PKS assemblies, there are several such multifunctional proteins assembled to result in the end product polyketide. (Cortes, J. et al., *Nature* (1990) 348:176; Donadio, S. et al., *Science* (1991) 252:675; MacNeil, D. J. et al., *Gene* (1992) 115:119.)

A number of modular PKS genes have been cloned. U.S. Pat. No. 5,252,474 describes cloning of genes encoding the synthase for avermectin; U.S. Pat. No. 5,098,837 describes the cloning of genes encoding the synthase for spiramycin; European application 791,655 and European application 791,656 describe the genes encoding the synthases for tylosin and platenolide respectively.

The PKS for erythromycin, used as an illustrative system is a modular PKS. Erythromycin was originally isolated from *S. erythraeus* (since reclassified as *Saccharopolyspora erythraea*) which was found in a soil sample from the Philippine archipelago. Cloning the genes was described by Donadio, S. et al., *Science* (1991) 252:675. The particulars have been reviewed by Perun, T. J. in *Drug Action and Drug Resistance in Bacteria,* Vol. 1, S. Mitsuhashi (ed.) University Park Press, Baltimore, 1977. The antibiotic occurs in various glycosylated forms, designated A, B, C, and D during various stages of fermentation. The entire erythromycin biosynthetic gene cluster from *S. erythraeus* has been mapped and sequenced by Donadio et al. in *Industrial Microorganisms: Basic and Applied Molecular Genetics* (1993) R. H. Baltz, G. D. Hegeman, and P. L. Skatrud (eds.) (*Amer Soc Microbiol*) and the entire PKS is an assembly of three such multifunctional proteins usually designated DEBS-1, DEBS-2, and DEBS-3, encoded by three separate genes.

Expression of the genes encoding the PKS complex may not be sufficient to permit the production by the synthase enzymes of polyketides when the genes are transformed into host cells that do not have the required auxiliary phosphopantetheinyl transferase enzymes which posttranslationally modify the ACP domains of the PKS. Genes encoding some of these transferases are described in WO97/13845. In addition, enzymes that mediate glycosylation of the polyketides synthesized are described in WO97/23630. U.S. Ser. No. 08/989,332 filed 11 Dec. 1997, now U.S. Pat. No. 6,033,883, describes the production of polyketides in hosts that normally do not produce them by supplying appropriate phosphopantetheinyl transferase expression systems. The contents of this application are incorporated herein by reference.

There have been attempts to alter the polyketide synthase pathway of modular PKS clusters. For example, European application 238,323 describes a process for enhancing production of polyketides by introducing a rate-limiting synthase gene and U.S. Pat. No. 5,514,544 describes use of an activator protein for the synthase in order to enhance production. U.S. Pat. Nos. 4,874,748 and 5,149,639 describe shuffle vectors that are useful in cloning modular PKS genes in general. Methods of introducing an altered gene into a microorganism chromosome are described in WO93/13663. Modification of the loading module for the DEBS-1 protein of the erythromycin-producing polyketide synthase to substitute the loading module for the avermectin-producing polyketide synthase in order to vary the starter unit was described by Marsden, Andrew F. A. et al. *Science* (1998) 279:199–202 and Oliynyk, M. et al. *Chemistry and Biology* (1996) 3:833–839. WO 98/01571, published 15 Jan. 1998, describes manipulation of the erythromycin PKS and polyketides resulting from such manipulation. In addition, WO 98/01546, also published 15 Jan. 1998 describes a hybrid modular PKS gene for varying the nature of the starter and extender units to synthesize polyketides.

In addition, U.S. Pat. Nos. 5,063,155 and 5,168,052 describe preparation of antibiotics using modular PKS systems. A number of modular PKS have been cloned. See, e.g., U.S. Pat. No. 5,098,837, EP 791,655, EP 791,656 and U.S. Pat. No. 5,252,474.

Type II PKS, in contrast to modular PKS, include several proteins, each of which is simpler than those found in Type I polyketide synthases. The active sites in these enzymes are used iteratively so that the proteins themselves are generally monofunctional or bifunctional. For example, the aromatic PKS complexes derived from *Streptomyces* have so far been found to contain three proteins encoded in three open reading frames. One protein provides ketosynthase (KS) and acyltransferase (AT) activities, a second provides a chain length determining factor (CLDF) and a third is an acyl carrier protein (ACP).

The present invention is concerned with PKS systems derived from modular PKS gene clusters. The nature of these clusters and their manipulation are further described below.

DISCLOSURE OF THE INVENTION

The invention provides recombinant materials for the production of combinatorial libraries of polyketides wherein the polyketide members of the library are synthesized by various PKS systems derived from naturally occurring PKS systems by using these systems as scaffolds. Generally, many members of these libraries may themselves be novel compounds, and the invention further includes novel polyketide members of these libraries. The invention methods may thus be directed to the preparation of an individual polyketide. The polyketide may or may not be novel, but the method of preparation permits a more convenient method of preparing it. The resulting polyketides may be further modified to convert them to antibiotics, typically through glycosylation. The invention also includes methods to recover novel polyketides with desired binding activities by screening the libraries of the invention.

Thus, in one aspect, the invention is directed to a method to prepare a nucleic acid which contains a nucleotide sequence encoding a modified polyketide synthase. The method comprises using a naturally occurring PKS encoding sequence as a scaffold and modifying the portions of the nucleotide sequence that encode enzymatic activities, either by mutagenesis, inactivation, or replacement. The thus modified nucleotide sequence encoding a PKS can then be used to modify a suitable host cell and the cell thus modified employed to produce a polyketide different from that produced by the PKS whose scaffolding has been used to support modifications of enzymatic activity. The invention is also directed to polyketides thus produced and the antibiotics to which they may then be converted.

In another aspect, the invention is directed to a multiplicity of cell colonies comprising a library of colonies wherein each colony of the library contains an expression vector for the production of a different modular PKS, but derived from a naturally occurring PKS. In a preferred embodiment, the different PKS are derived from the erythromycin PKS. In any case, the library of different modular PKS is obtained by modifying one or more of the regions of a naturally occurring gene or gene cluster encoding an enzymatic activity so as to alter that activity, leaving intact the scaffold portions of the naturally occurring gene. If desired, more than one scaffold source may be used, but basing the cluster of modules on a single scaffold is preferred. In another aspect, the invention is directed to a multiplicity of cell colonies comprising a library of colonies wherein each colony of the library contains a different modular PKS derived from a naturally occurring PKS, preferably the erythromycin PKS. The invention is also directed to methods to produce libraries of PKS complexes and to produce libraries of polyketides by culturing these colonies, as well as to the libraries so produced. In addition, the invention is directed to methods to screen the resulting polyketide libraries and to novel polyketides contained therein.

DETAILED DESCRIPTION OF THE INVENTION

It may be helpful to review the nature of the erythromycin PKS complex and the gene cluster that encodes it as a model for modular PKS, in general.

Figure 1A:
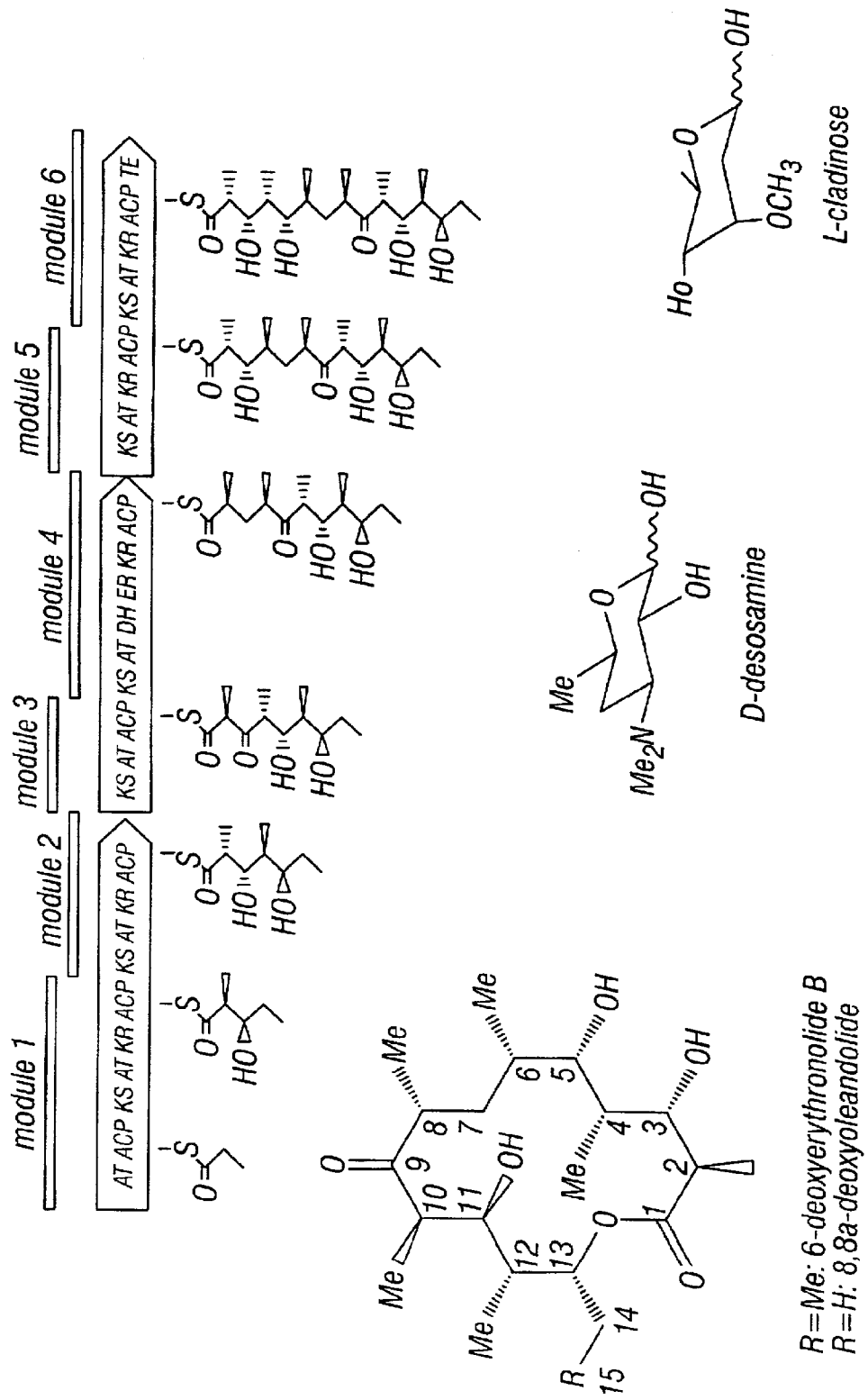
FIG. 1A is a diagram of the erythromycin PKS complex from *S. erythraeus* showing the function of each multifunctional protein, and also shows the structure of 6-deoxyerythronolide B and of D-desosamine and L-cladinose.

FIG. 1A is a diagrammatic representation of the gene cluster encoding the synthase for the polyketide backbone of the antibiotic erythromycin. The erythromycin PKS protein assembly contains three high-molecular-weight proteins (>200 kD) designated DEBS-1, DEBS-2 and DEBS-3, each encoded by a separate gene (Caffrey et al., *FEBS Lett* (1992) 304:225). The diagram in FIG. 1A shows that each of the three proteins contains two modules of the synthase—a module being that subset of reactivities required to provide an additional 2-carbon unit to the molecule. As shown in FIG. 1A, modules 1 and 2 reside on DEBS-1; modules 3 and 4 on DEBS-2 and modules 5 and 6 on DEBS-3. The minimal module is typified in module 3 which contains a ketosynthase (KS), an acyltransferase (AT) and an acyl carrier protein (ACP). These three functions are sufficient to activate an extender unit and attach it to the remainder of the growing molecule. Additional activities that may be included in a module relate to reactions other than the Claisen condensation, and include a dehydratase activity (DH), an enoylreductase activity (ER) and a ketoreductase activity (KR). The first module also contains repeats of the AT and ACP activities because it catalyzes the initial condensation, i.e. it begins with a "loading domain" represented by AT and ACP, which determine the nature of the starter unit. Although not shown, module 3 has a KR region which has been inactivated by mutation. The "finishing" of the molecule is regulated by the thioesterase activity (TE) in module 6. This thioesterase appears to catalyze cyclization of the macrolide ring thereby increasing the yield of the polyketide product.

Figure 1B:
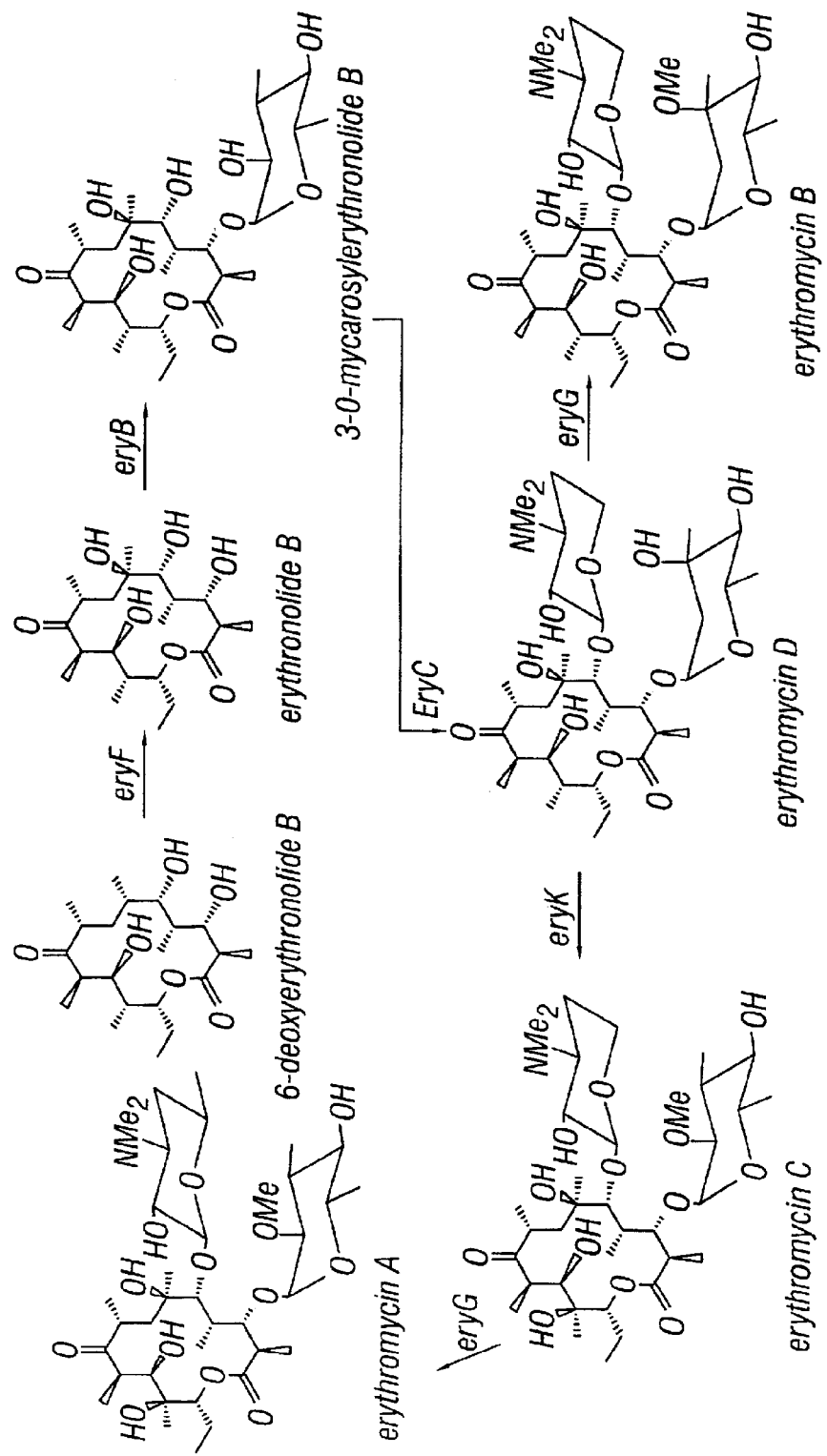
FIG. 1B shows a diagram of the post-PKS biosynthesis of erythromycins A–D.

The product in this case is 6dEB; the structure and numbering system for this molecule are shown in FIG. 1A. Conversion to the antibiotics erythromycin A, B, C and D would require glycosylation generally by D-desosamine or L-mycarose, which is converted to cladinose in erythromycins A and B. FIG. 1B diagrams the post-PKS biosynthesis of the erythromycins through addition of glycosyl groups.

As shown, 6dEB is converted by the gene eryF to erythronolide B which is, in turn, glycosylated by eryB to obtain 3-O-mycarosylerythronolide B which contains L-mycarose at C-3. The enzyme eryC then converts this compound to erythromycin D by glycosylation with D-desosamine at C-5. Erythromycin D, therefore, differs from 6dEB through glycosylation and by the addition of a hydroxyl group at C-6. Erythromycin D can be converted to erythromycin B in a reaction catalyzed by eryG by methylating the L-mycarose residue at C-3. Erythromycin D is converted to erythromycin C by the addition of a hydroxyl group at C-12. Erythromycin A is obtained from erythromycin C by methylation of the mycarose residue catalyzed by eryG. The series of erythromycin antibiotics, then, differs by the level of hydroxylation of the polyketide framework and by the methylation status of the glycosyl residues.

Figure 2:
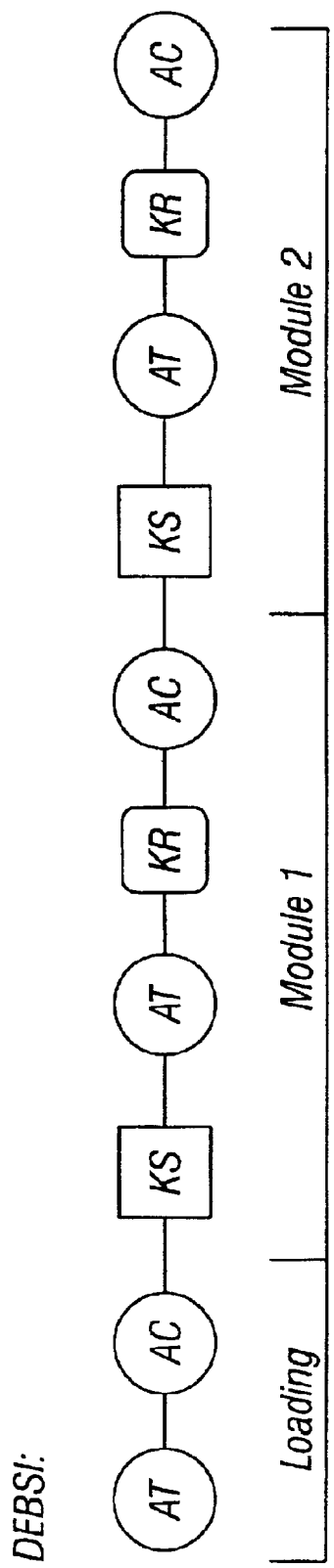
FIG. 2 is a diagram of DEBS-1 from *S. erythraeus* showing the functional regions separated by linker regions.
Figure 2:
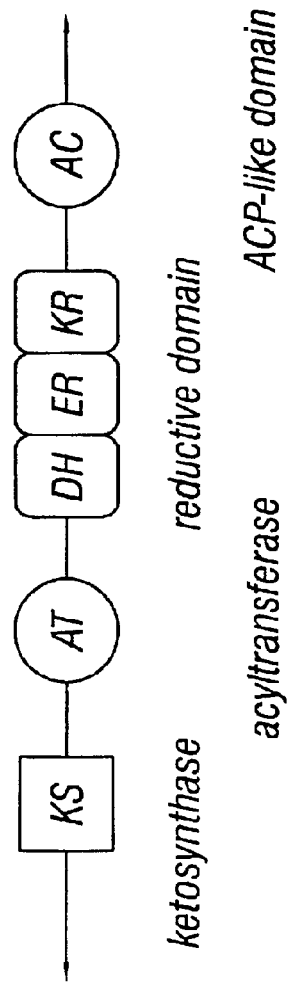

FIG. 2 shows a detailed view of the regions in the first two modules which comprise the first open reading frame encoding DEBS-1. The regions that encode enzymatic activities are separated by linker or "scaffold"-encoding regions. These scaffold regions encode amino acid sequences that space the enzymatic activities at the appropriate distances and in the correct order. Thus, these linker regions collectively can be considered to encode a scaffold into which the various activities are placed in a particular order and spatial arrangement. This organization is similar in the remaining genes, as well as in other naturally occurring modular PKS gene clusters.

The three DEBS-1, 2 and 3 proteins are encoded by the genetic segments eryAI, eryAII and eryAIII, respectively. These reading frames are located on the bacterial chromosome starting at about 10 kb distant from the erythromycin resistance gene (ermE or eryR).

The detailed description above referring to erythromycin is typical for modular PKS in general. Thus, rather than the illustrated erythromycin, the polyketide synthases making up the libraries of the invention can be derived from the synthases of other modular PKS, such as those which result in the production of rapamycin, avermectin, FK-506, FR-008, monensin, rifamycin, soraphen-A, spinocyn, squalestatin, or tylosin, and the like.

Regardless of the naturally occurring PKS gene used as a scaffold, the invention provides libraries or individual modified forms, ultimately of polyketides, by generating modifications in the erythromycin PKS or other naturally occurring PKS gene cluster so that the protein complexes produced by the cluster have altered activities in one or more respects, and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. All of the PKS encoding sequences used in the present invention represent modular polyketide synthases "derived from" a naturally occurring PKS, illustrated by the erythromycin PKS. As will be further described below, the metes and bounds of this derivation can be described on both the protein level and the encoding nucleotide sequence level.

By a modular PKS "derived from" the erythromycin or other naturally occurring PKS is meant a modular polyketide synthase (or its corresponding encoding gene(s)) that retains the scaffolding of all of the utilized portion of the naturally occurring gene. (Not all modules need be included in the constructs.) On the constant scaffold, at least one enzymatic activity is mutated, deleted or replaced, so as to alter the activity. Alteration results when these activities are deleted or are replaced by a different version of the activity, or simply mutated in such a way that a polyketide other than the natural product results from these collective activities. This occurs because there has been a resulting alteration of the starter unit and/or extender unit, and/or stereochemistry, and/or chain length or cyclization and/or reductive or dehydration cycle outcome at a corresponding position in the product polyketide. Where a deleted activity is replaced, the origin of the replacement activity may come from a corresponding activity in a different naturally occurring polyketide synthase or from a different region of the same PKS. In the case of erythromycin, for example, any or all of the DEBS-1, DEBS-2 and DEBS-3 proteins may be included in the derivative or portions of any of these may be included; but the scaffolding of an erythromycin PKS protein is retained in whatever derivative is considered. Similar comments pertain to the corresponding ery-AI, ery-AII and ery-AIII genes.

The derivative may contain preferably at least a thioesterase activity from the erythromycin or other naturally occurring PKS gene cluster.

In summary, a polyketide synthase "derived from" a naturally occurring PKS contains the scaffolding encoded by all or the portion employed of the naturally occurring synthase gene, contains at least two modules that are functional, preferably three modules, and more preferably four or more modules and contains mutations, deletions, or replacements of one or more of the activities of these functional modules so that the nature of the resulting polyketide is altered. This definition applies both at the protein and genetic levels. Particular preferred embodiments include those wherein a KS, AT, KR, DH or ER has been deleted or replaced by a version of the activity from a different PKS or from another location within the same PKS. Also preferred are derivatives where at least one noncondensation cycle enzymatic activity (KR, DH or ER) has been deleted or wherein any of these activities has been mutated so as to change the ultimate polyketide synthesized.

Thus, there are five degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methylmalonyl, or ethylmalonyl, etc. Third, the loading domain specificity will also have an effect on the resulting carbon skeleton of the polyketide. Thus, the loading domain may use a different starter unit, such as acetyl, propionyl, and the like. Fourth, the oxidation state at various positions of the polyketide will be determined by the dehydratase and reductase portions of the modules. This will determine the presence and location of ketone, alcohol, double bonds or single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase since the dehydratase would abolish chirality. Second, the specificity of the ketoreductase will determine the chirality of any β-OH. Finally, the enoyl reductase specificity for substituted malonyls as extender units will influence the result when there is a complete KR/DH/ER available.

In the working examples below, the foregoing variables for varying loading domain specificity which controls the starter unit, a useful approach is to modify the KS activity in module 1 which results in the ability to incorporate alternative starter units as well as module 1 extended units. This approach was illustrated in PCT application US/96/11317, published 23 Jan. 1997. as WO 97/02358, wherein the KS-I activity was inactivated through mutation. Polyketide synthesis is then initiated by feeding chemically synthesized analogs of module 1 diketide products. Working examples of this aspect are also presented hereinbelow.

Thus, the modular PKS systems, and in particular, the erythromycin PKS system, permit a wide range of polyketides to be synthesized. As compared to the aromatic PKS systems, a wider range of starter units including aliphatic monomers (acetyl, propionyl, butyryl, isovaleryl, etc.), aromatics (aminohydroxybenzoyl), alicyclics (cyclohexanoyl), and heterocyclics (thiazolyl) are found in various macrocyclic polyketides. Recent studies have shown that modular PKSs have relaxed specificity for their starter units (Kao et al. *Science* (1994), supra). Modular PKSs also exhibit considerable variety with regard to the choice of extender units in each condensation cycle. The degree of β-ketoreduction following a condensation reaction has also been shown to be altered by genetic manipulation (Donadio et al. *Science* (1991), supra; Donadio, S. et al. *Proc Natl Acad Sci USA* (1993) 90:7119–7123). Likewise, the size of the polyketide product can be varied by designing mutants with the appropriate number of modules (Kao, C. M. et al. *J Am Chem Soc* (1994) 116:11612–11613). Lastly, these enzymes are particularly well-known for generating an impressive range of asymmetric centers in their products in a highly controlled manner. The polyketides and antibiotics produced by the methods of the present invention are typically single stereoisomeric forms. Although the compounds of the invention can occur as mixtures of stereoisomers, it is more practical to generate individual stereoisomers using this system. Thus, the combinatorial potential within modular PKS pathways based on any naturally occurring modular, such as the erythromycin, PKS scaffold is virtually unlimited.

In general, the polyketide products of the PKS must be further modified, typically by glycosylation, in order to exhibit antibiotic activity. Methods for glycosylating the polyketides are generally known in the art; the glycosylation may be effected intracellularly by providing the appropriate glycosylation enzymes or may be effected in vitro using chemical synthetic means.

The antibiotic modular polyketides may contain any of a number of different sugars, although D-desosamine, or a close analog thereof, is most common. Erythromycin, picromycin, narbomycin and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al. *J Am Chem Soc* (1975) 97:3512, 3513. Other, apparently more stable, donors include glycosyl fluorides, thioglycosides, and trichloroacetimidates; Woodward, R. B. et al. *J Am Chem Soc* (1981) 103:3215; Martin, S. F. et al. *Am Chem Soc* (1997) 119:3193; Toshima, K. et al. *J Am Chem Soc* (1995) 117:3717; Matsumoto, T. et al. *Tetrahedron Lett* (1988) 29:3575. Glycosylation can also be effected using the macrolides as starting materials and using mutants of *S. erythraea* that are unable to synthesize the macrolides to make the conversion. A method is illustrated in the Examples hereinbelow.

Methods to Construct Multiple Modular PKS Derived from a Naturally Occurring PKS The derivatives of a naturally occurring PKS can be prepared by manipulation of the relevant genes. A large number of modular PKS gene clusters have been mapped and/or sequenced, including erythromycin, soraphen A, rifamycin, and rapamycin, which have been completely mapped and sequenced, and FK506 and oleandomycin which have been partially sequenced, and candicidin, avermectin, and nemadectin which have been mapped and partially sequenced. Additional modular PKS gene clusters are expected to be available as time progresses. These genes can be manipulated using standard techniques to delete or inactivate activity encoding regions, insert regions of genes encoding corresponding activities from the same or different PKS system, or otherwise mutated using standard procedures for obtaining genetic alterations. Of course, portions of, or all of, the desired derivative coding sequences can be synthesized using standard solid phase synthesis methods such as those described by Jay, E., et al., *J Biol Chem* (1984) 259:6331 and which are available commercially from, for example, Applied Biosystems, Inc.

In order to obtain nucleotide sequences encoding a variety of derivatives of the naturally occurring PKS, and thus a variety of polyketides for construction of a library, a desired number of constructs can be obtained by "mixing and matching" enzymatic activity-encoding portions, and mutations can be introduced into the native host PKS gene cluster or portions thereof.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:448; Geisselsoder et al. *BioTechniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc Natl Acad Sci USA* (1982) 79:6409. PCR mutagenesis will also find use for effecting the desired mutations.

Random mutagenesis of selected portions of the nucleotide sequences encoding enzymatic activities can be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER would correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication WO 96/40968.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into host vectors, the resulting vectors transformed or transfected into host cells and the resulting cells plated out into individual colonies.

Suitable control sequences include those which function in eucaryotic and procaryotic host cells. Preferred hosts include fungal systems such as yeast and procaryotic hosts, but single cell cultures of, for example, mammalian cells could also be used. There is no particular advantage, however, in using such systems. Particularly preferred are yeast and procaryotic hosts which use control sequences compatible with *Streptomyces* spp. Suitable controls sequences for single cell cultures of various types of organisms are well known in the art. Control systems for expression in yeast, including controls which effect secretion are widely available and routinely used. Control elements include promoters, optionally containing operator sequences, and other elements depending on the nature of the host, such as ribosome binding sites. Particularly useful promoters for procaryotic hosts include those from PKS gene clusters which result in the production of polyketides as secondary metabolites, including those from aromatic (Type II) PKS gene clusters. Examples are act promoters, tcm promoters, spiramycin promoters, and the like. However, other bacterial promoters, such as those derived from genes that encode sugar metabolizing enzymes, such as from galactose, lactose (lac) and maltose, are also useful. Additional examples include promoters derived from genes that encode biosynthetic enzymes for compounds such as tryptophan (trp), and the β-lactamase (bla), bacteriophage lambda PL, and T5 promoters. In addition, synthetic promoters, such as the tac promoter (U.S. Pat. No. 4,551,433), can be used.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for screening cells successfully transformed by the present constructs.

The various PKS nucleotide sequences, or a cocktail of such sequences, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR.

As described above, particularly useful control sequences are those which themselves, or using suitable regulatory systems, activate expression during transition from growth to stationary phase in the vegetative mycelium. The system contained in the illustrated plasmid pCK7, i.e., the actI/actIII promoter pair and the actII-ORF4, an activator gene, is particularly preferred. Particularly preferred hosts are those which lack their own means for producing polyketides so that a cleaner result is obtained. Illustrative host cells of this type include the modified *S. coelicolor* CH999 culture described in PCT publication WO 96/40968 and similar strains of *S. lividans*.

The expression vectors containing nucleotide sequences encoding a variety of PKS systems for the production of different polyketides are then transformed into the appropriate host cells to construct the library. In one straightforward approach, a mixture of such vectors is transformed into the selected host cells and the resulting cells plated into individual colonies and selected for successful transformants. Each individual colony will then represent a colony with the ability to produce a particular PKS synthase and ultimately a particular polyketide. Typically, there will be duplications in some of the colonies; the subset of the transformed colonies that contains a different PKS in each member colony can be considered the library. Alternatively, the expression vectors can be used individually to transform hosts, which transformed hosts are then assembled into a library. A variety of strategies might be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length allow quite large libraries.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation.

As disclosed in copending application Ser. No. 08/989, 332 filed 11 Dec. 1997, incorporated herein by reference, a wide variety of hosts can be used, even though some hosts natively do not contain the appropriate post-translational mechanisms to activate the acyl carrier proteins of the synthases. These hosts can be modified with the appropriate recombinant enzymes to effect these modifications.

The polyketide producing colonies can be identified and isolated using known techniques and the produced polyketides further characterized. The polyketides produced by these colonies can be used collectively in a panel to represent a library or may be assessed individually for activity.

The libraries can thus be considered at four levels: (1) a multiplicity of colonies each with a different PKS encoding sequence encoding a different PKS cluster but all derived from a naturally occurring PKS cluster; (2) colonies which contain the proteins that are members of the PKS produced by the coding sequences; (3) the polyketides produced; and (4) antibiotics derived from the polyketides. Of course, combination libraries can also be constructed wherein members of a library derived, for example, from the erythromycin PKS can be considered as a part of the same library as those derived from, for example, the rapamycin PKS cluster.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art.

Alternatively, individual polyketide members of the library can be tested against a desired target. In this event, screens wherein the biological response of the target is measured can more readily be included.

Indeed, a large number of novel polyketides have been prepared according to the method of the invention as illustrated in the examples below. These novel polyketides are useful intermediates in formation of compounds with antibiotic activity through glycosylation reactions as described above. As indicated above, the individual polyketides are reacted with suitable sugar derivatives to obtain compounds with antibiotic activity. Antibiotic activity can be verified using typical screening assays such as those set forth in Lehrer, R. et al. *J Immunol Meth* (1991) 137:167–173.

New polyketides which are the subject of the invention are those described below. New antibiotics which are the subject of the invention include the glycosylated forms of these polyketides.

In one embodiment, the polyketides of the invention include the compounds of structure (1) and the glycosylated forms thereof. The compounds include the polyketide structure:

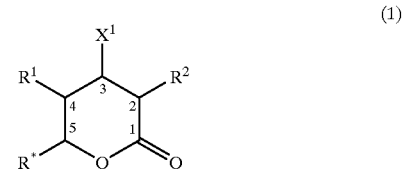

Figure 6A:
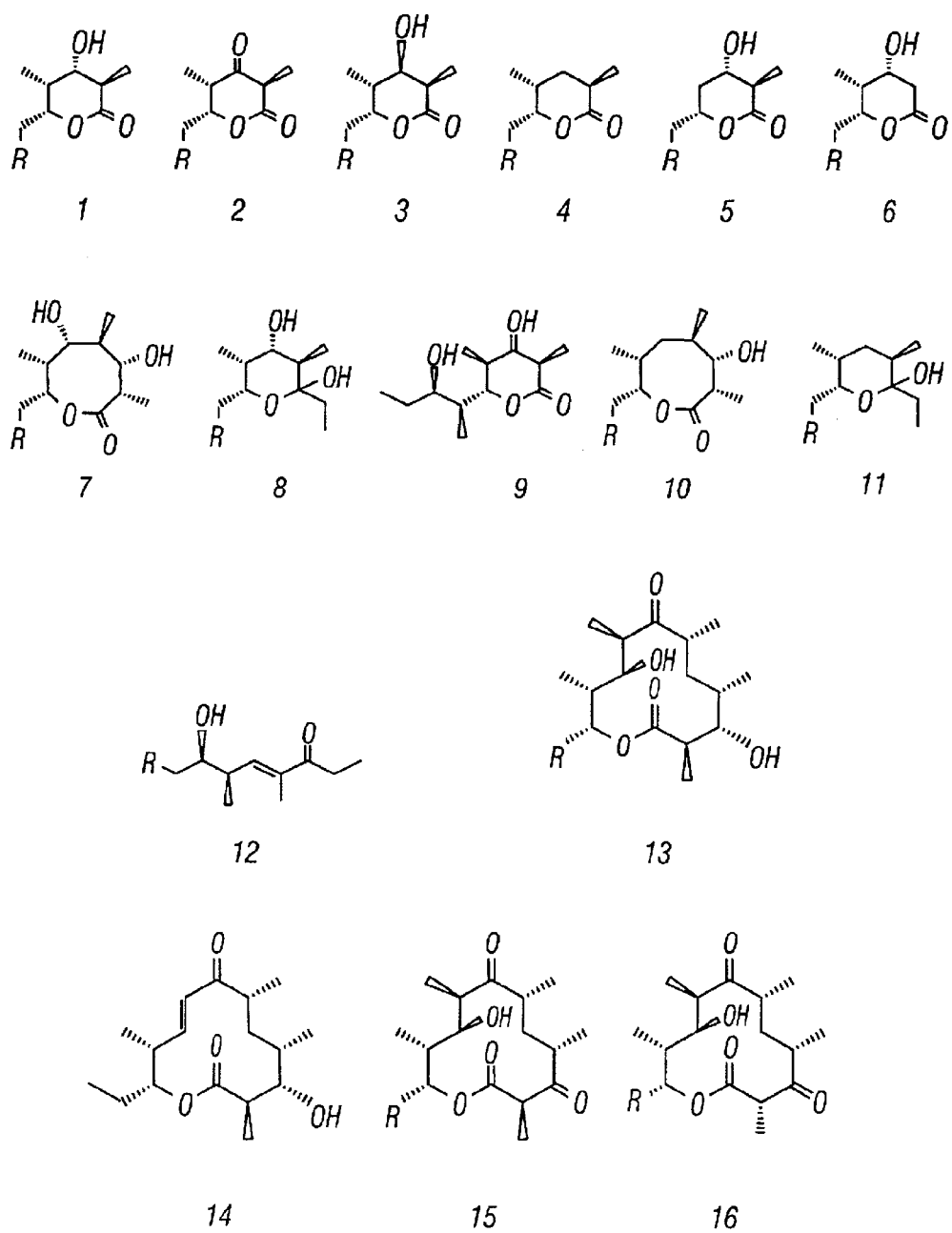
FIGS. 6A–6H show the structures of polyketides produced by manipulating the erythromycin PKS gene cluster.

(1)

including the isolated stereoisomeric forms thereof;

wherein R* is a straight chain, branched or cyclic, saturated or unsaturated substituted or unsubstituted hydrocarbyl of 1–15C;

each of $R^1$ and $R^2$ is independently H or alkyl (1–4C) wherein any alkyl at $R^1$ may optionally be substituted;

$X^1$ is $H_2$, HOH or $=O$;

with the provisos that:

at least one of $R^1$ and $R^2$ must be alkyl (1–4C); and the compound is other than compounds 1, 2, 3, 5 and 6 of FIG. 6A.

In another embodiment, the polyketides of the invention include the compounds of formula (2) and the glycosylated forms thereof. These compounds include the polyketide structure:

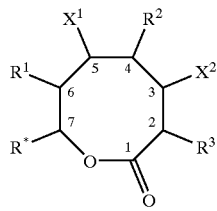

(2)

including the isolated stereoisomeric forms thereof;

wherein R* is a straight chain, branched or cyclic, saturated or unsaturated substituted or unsubstituted hydrocarbyl of 1–15C;

each of $R^1$, $R^2$ and $R^3$ is independently H or alkyl (1–4C) wherein any alkyl at $R^1$ may optionally be substituted;

each of $X^1$ and $X^2$ is independently $H_2$, HOH or =O;

with the provisos that:

at least two of $R^1$, $R^2$ and $R^3$ are alkyl (1–4C).

In another embodiment, the polyketides of the invention include the compounds of structure (3) and the glycosylated forms thereof. The compounds include the polyketide structure:

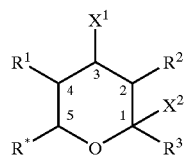

(3)

including the isolated stereoisomeric forms thereof;

wherein R* is a straight chain, branched or cyclic, saturated or unsaturated substituted or unsubstituted hydrocarbyl of 1–15C;

each of $R^1$, $R^2$ and $R^3$ is independently H or alkyl (1–4C) wherein any alkyl at $R^1$ may optionally be substituted;

each of $X^1$ and $X^2$ is independently $H_2$, HOH or =O;

with the provisos that:

at least one of $R^1$ and $R^2$ must be alkyl (1–4C); and the compound is other than compound 8 of FIG. 6A.

The antibiotic forms of the polyketide of formula (3) are the corresponding glycosylated forms.

Still other embodiments are those of the following formula, including the glycosylated forms thereof. These are derived from the compound of formula (4) which has the structure:

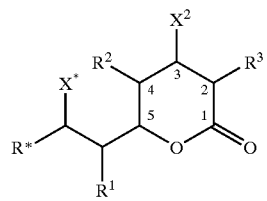

(4)

including the isolated stereoisomeric forms thereof;

wherein R* is a straight chain, branched or cyclic, saturated or unsaturated substituted or unsubstituted hydrocarbyl of 1–15C;

each of $R^1$, $R^2$ and $R^3$ is independently H or alkyl (1–4C) wherein any alkyl at $R^1$ may optionally be substituted;

each of X* and $X^2$ is independently $H_2$, HOH or =O;

with the provisos that:

at least one of $R^2$ and $R^3$ is alkyl (1–4C); and the compound is other than compound 9 of FIG. 6A.

Still other embodiments are the result of the condensation of five modules of the polyketide synthase system. The polyketide forms of these compounds are of the formula:

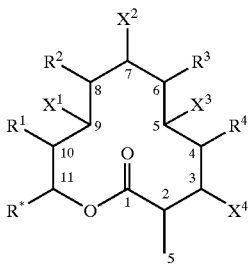

Figure 11:
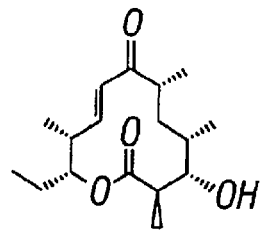
FIG. 11 shows the structures of known, previously produced, 12-member macrolides.
Figure 11:
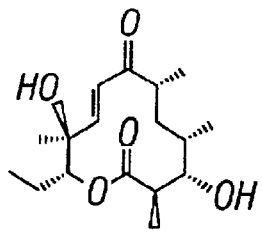
Figure 11:
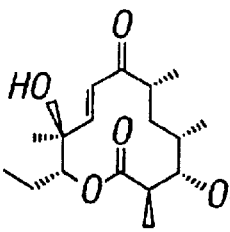
Figure 11:
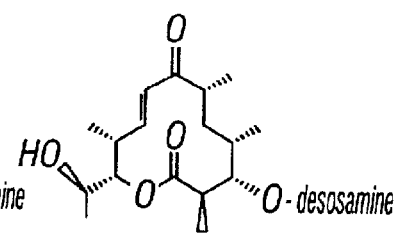
Figure 11:
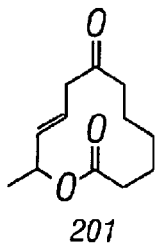
Figure 11:
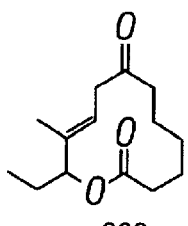
Figure 11:
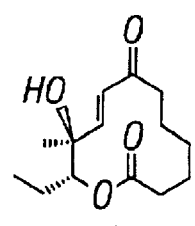
Figure 11:
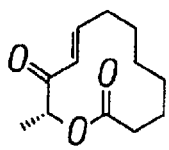
Figure 11:
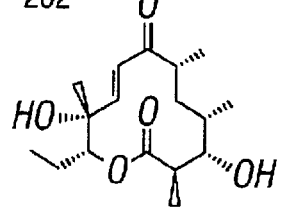
Figure 11:
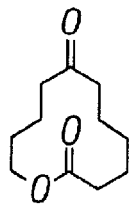
Figure 11:
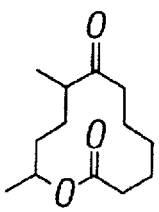
Figure 11:
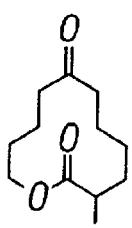
Figure 11:
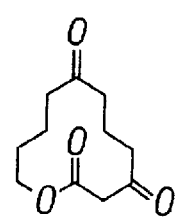

(5)

including the glycosylated and isolated stereoisomeric forms thereof;

wherein R* is a straight chain, branched or cyclic, saturated or unsaturated substituted or unsubstituted hydrocarbyl of 1–15C;

each of $R^1$, $R^2$, $R^3$, $R^4$ and $R^5$ is independently H or alkyl (1–4C) wherein any alkyl at $R^1$ may optionally be substituted;

each of $X^1$, $X^2$, $X^3$ and $X^4$ is independently $H_2$, HOH or =O; or $X^1$ or $X^2$ or $X^3$ or $X^4$ is H and the compound of formula (5) contains a π-bond at positions 8–9 or 6–7 or 4–5 or 2–3;

with the provisos that:

at least two of $R^1$–$R^5$ are alkyl (1–4C); and the compound is other than compound 13 or 14 of FIG. 6A or compound 205, 210–213 of FIG. 11.

Preferred forms of compounds of formula (5) are those wherein at least three, more preferably at least four, of $R^1$–$R^5$ are alkyl (1–4C), preferably methyl or ethyl.

Also preferred are compounds wherein $X^1$ is —OH and/or $X^2$ is =O, and/or $X^3$ is H.

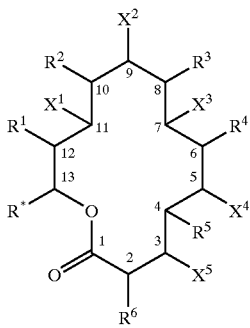

Figure 6B:
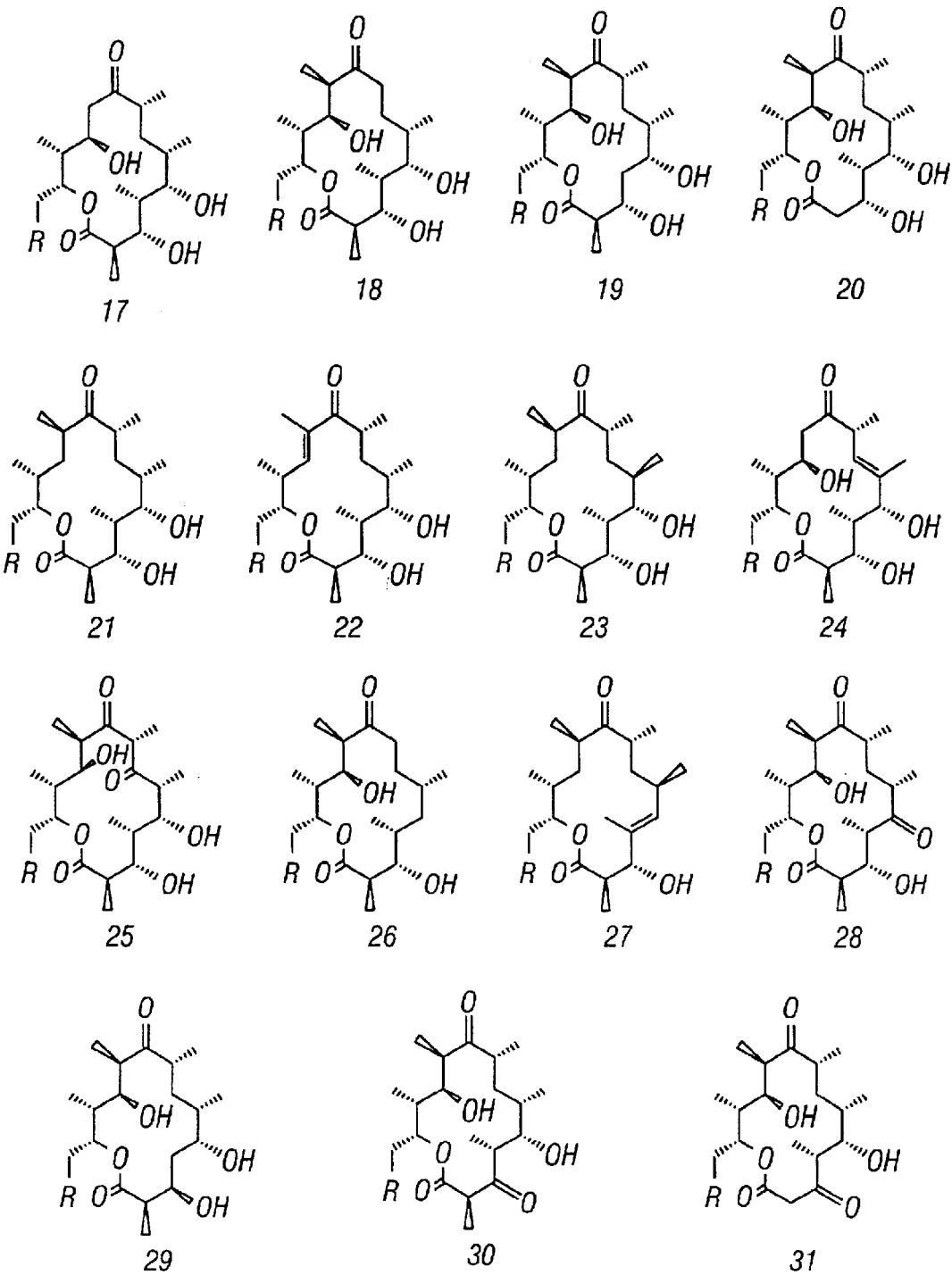
Figure 6C:
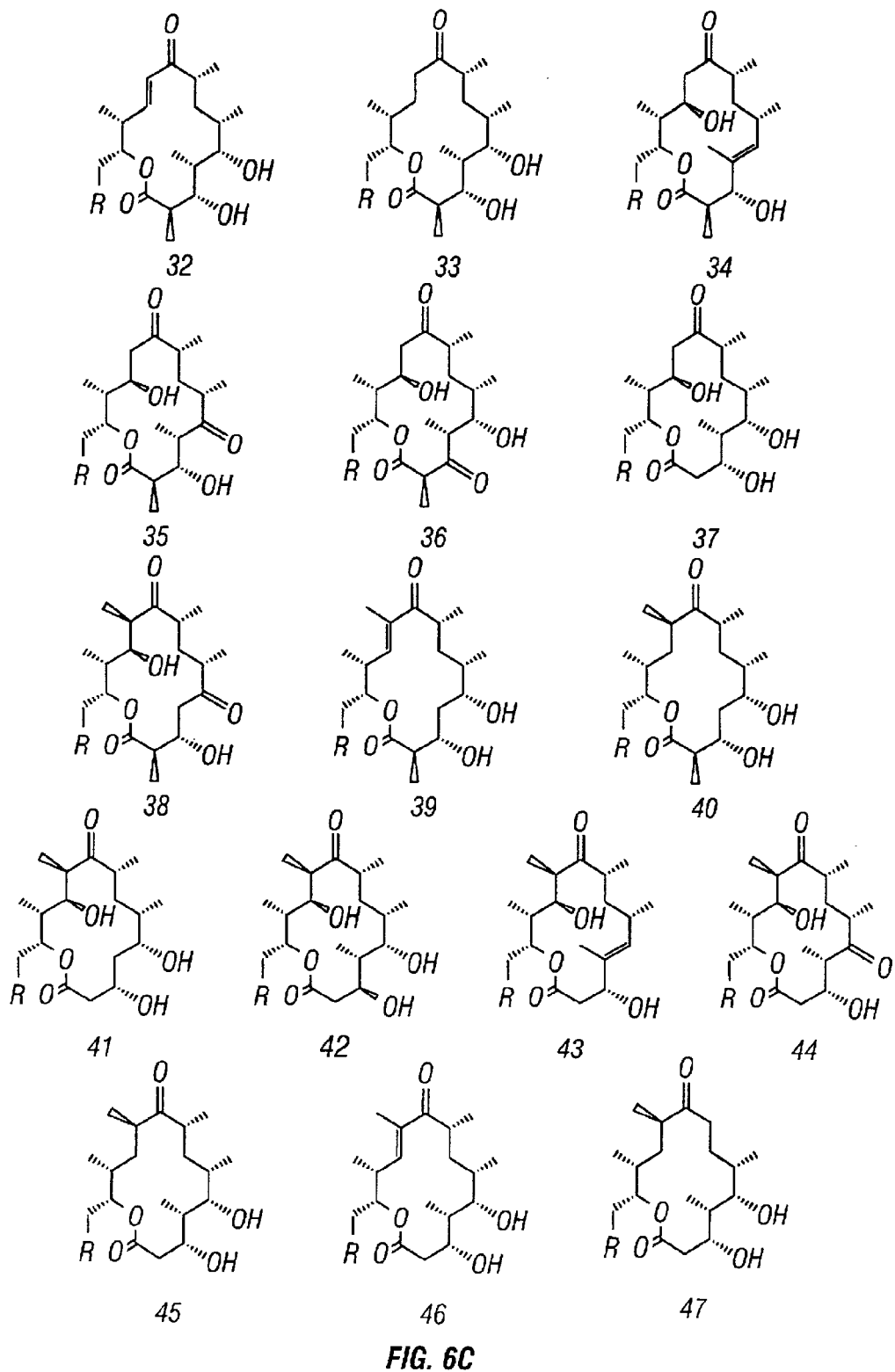
Figure 6D:
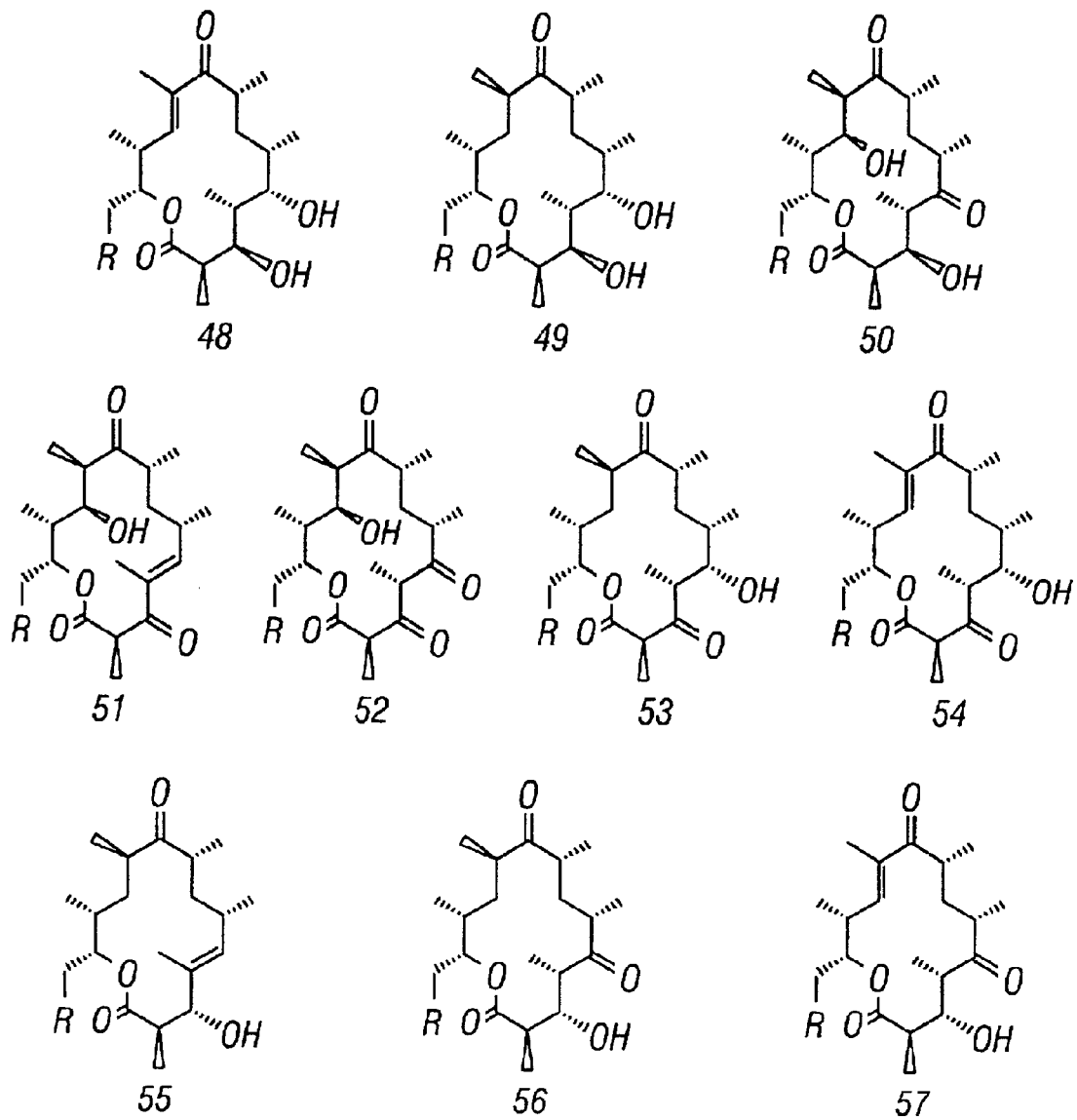
Figure 6E:
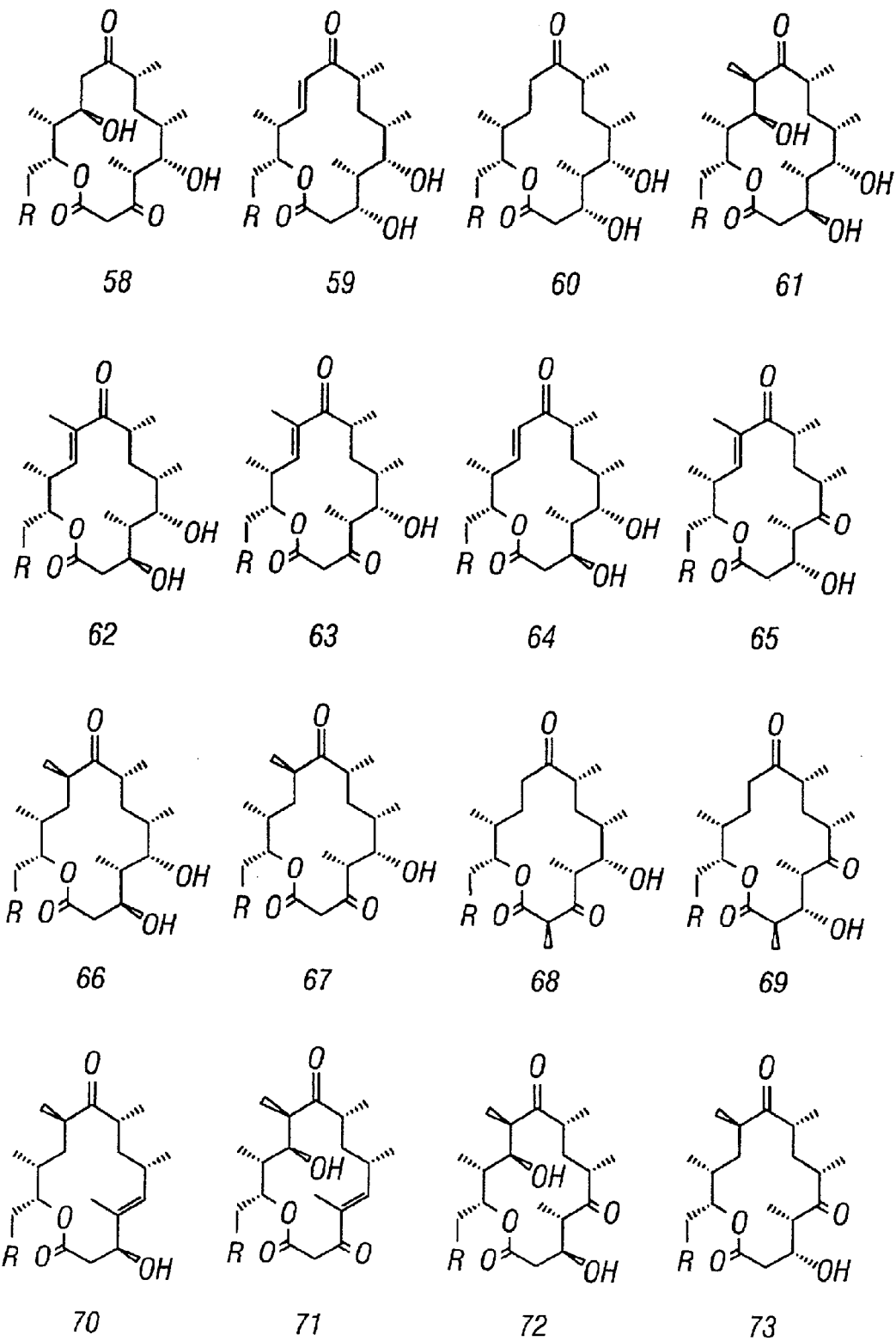
Figure 6F:
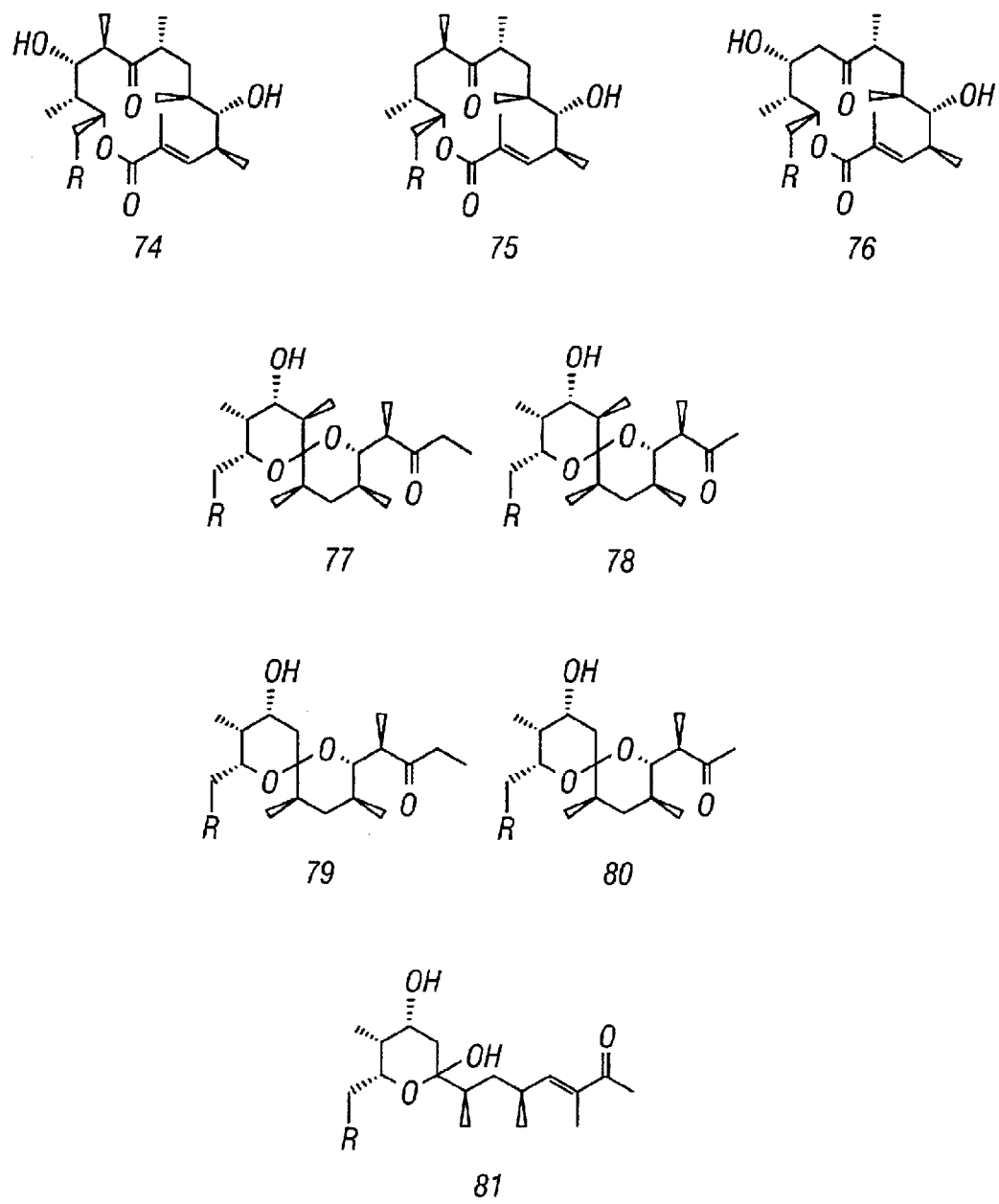
Figure 12A:
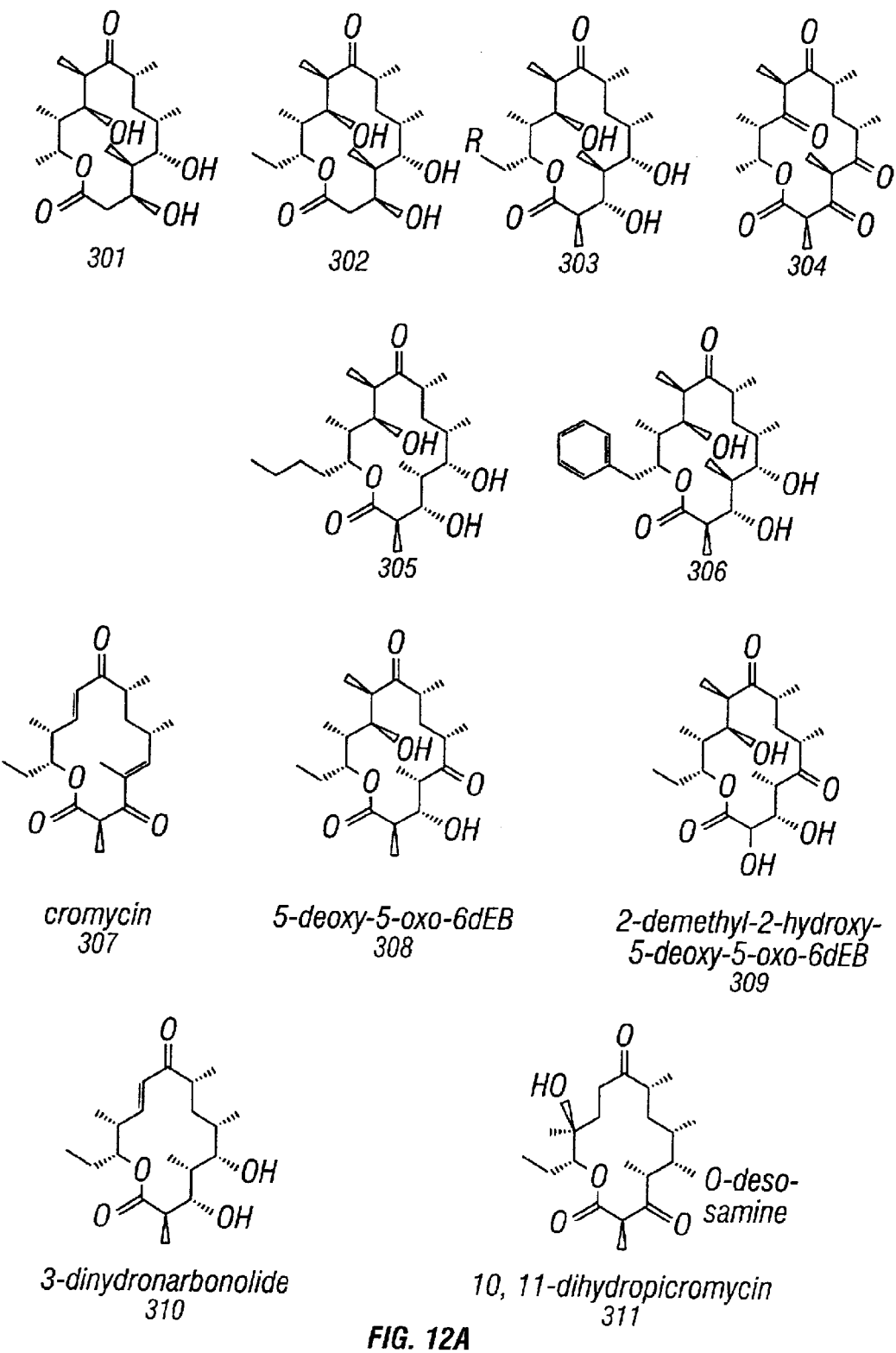
FIGS. 12A and 12B show the structures of known and previously produced 14-member macrolides.
Figure 12B:
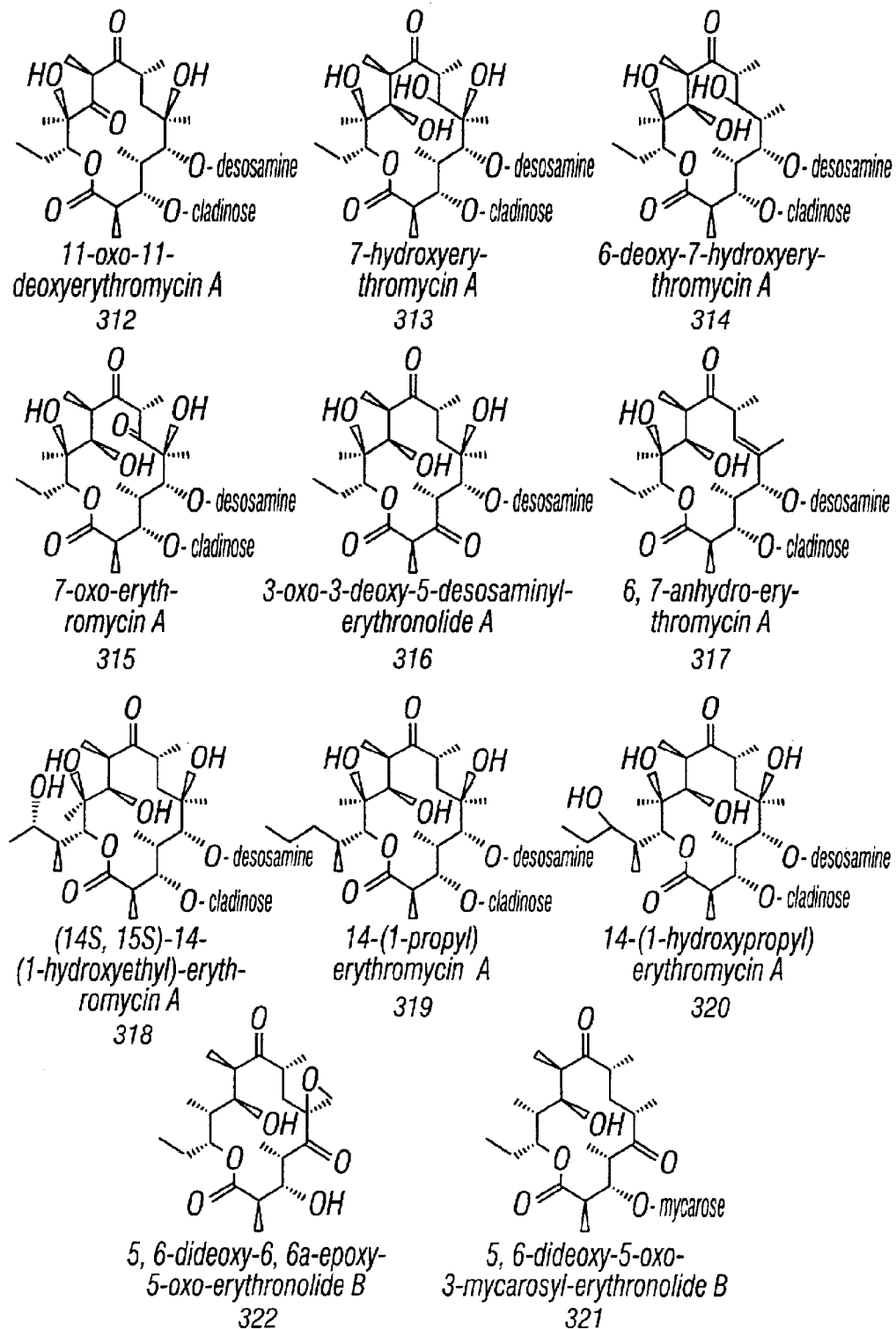

(6)

including the glycosylated and isolated stereoisomeric forms thereof;

wherein R* is a straight chain, branched or cyclic, saturated or unsaturated substituted or unsubstituted hydrocarbyl of 1–15C;

each of $R^1$–$R^6$ is independently H or alkyl (1–4C) wherein any alkyl at $R^1$ may optionally be substituted;

each of $X^1$–$X^5$ is independently $H_2$, HOH or =O; or each of $X^1$–$X^5$ is independently H and the compound of formula (5) contains a π-bond in the ring adjacent to the position of said X at 2–3, 4–5, 6–7, 8–9 and/or 10–11;

with the proviso that:

at least two of $R^1$–$R^6$ are alkyl (1–4C); and the compound is other than compound 17, 24 or 28 of FIG. 6B, compound 301–311 of FIG. 12(A) or compounds 312–322 of FIG. 12(B).

Preferred compounds comprising formula 6 are those wherein at least three of $R^1$–$R^5$ are alkyl (1–4C), preferably methyl or ethyl; more preferably wherein at least four of $R^1$–$R^5$ are alkyl (1–4C), preferably methyl or ethyl.

Also preferred are those wherein $X^2$ is $H_2$, =O or H▶OH, and/or $X^3$ is H, and/or $X^1$ is OH and/or $X^4$ is OH and/or $X^5$ is OH.

Particularly preferred are compounds of formulas 18–23, 25–27, 29–75 and 101 and 113 of FIGS. 6B–6F. Also preferred are compounds with variable R* when $R^1$–$R^5$ are methyl, $X^2$ is =O, and $X^1$, $X^4$ and $X^5$ are OH examples of which are depicted in formulas 96–100 and 104–107 of FIGS. 6G and 6H. The glycosylated forms of the foregoing are also preferred.

Other polyketides which result from the condensation catalyzed by six modules of a modular PKS include those of the formula:

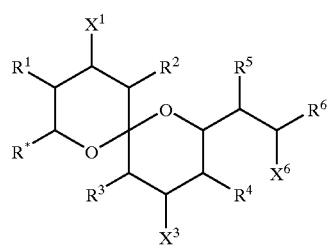

(7)

including the glycosylated and isolated stereoisomeric forms thereof, wherein R* is a straight chain, branched or cyclic, saturated or unsaturated substituted or unsubstituted hydrocarbyl of 1–15C;

each of $R^1$–$R^5$ is independently H or alkyl (1–4C) wherein any alkyl at $R^1$ may optionally be substituted;

$R^6$ is alkyl (1–5C);

each of $X^1$ and $X^3$ and $X^6$ is independently $H_2$, HOH or =O;

with the proviso that:

at least two of $R^1$–$R^4$ are alkyl (1–4C).

These and their corresponding glycosylated forms are also included in the invention.

Still others include those of the formula:

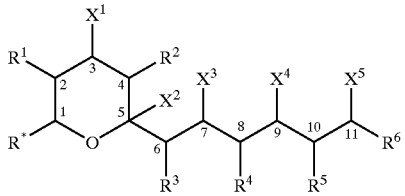

(8)

including the isolated stereoisomeric forms thereof;

wherein R* is a straight chain, branched or cyclic, saturated or unsaturated substituted or unsubstituted hydrocarbyl of 1–15C;

each of $R^1$–$R^5$ is independently H or alkyl (1–4C) wherein any alkyl at $R^1$ may optionally be substituted;

$R^6$ is alkyl (1–5C);

$X^2$ is OH or H;

each $X^1$, $X^3$, $X^4$ and $X^5$ is independently $H_2$, HOH or =O; or $X^3$ or $X^4$ is H and the compound of formula (8) has a π-bond between positions 7–8 or 9–10, with the proviso that:

if $X^2$ is H, at least one of $X^3$ and $X^4$ is HOH or =O.

These and their corresponding glycosylated forms are also included in the invention.

As above, the glycosylated forms are useful antibiotics.

As set forth above, R* in the compounds of the invention may be substituted as well as unsubstituted. Suitable substituents include halo (F, Cl, Br, I), $N_3$, OH, O-alkyl (1–6C), S-alkyl (1–6C), CN, O-acyl (1–7C), O-aryl (6–10C), O-alkyl-aryl (7–14C), $NH_2$, NH-alkyl (1–6C) and N-(alkyl)$_2$.

Suitable substituents on $R^1$ are selected from the same group as those for R* In addition, the substituents on $R^1$ and $R^*$ may form a ring system such as an epoxide ring, or a larger heterocyclic ring including O, or N or S. Preferred substituents for R* and $R^1$ are halo, OH and $NH_2$. Unsubstituted forms are also preferred.

Figure 8A:
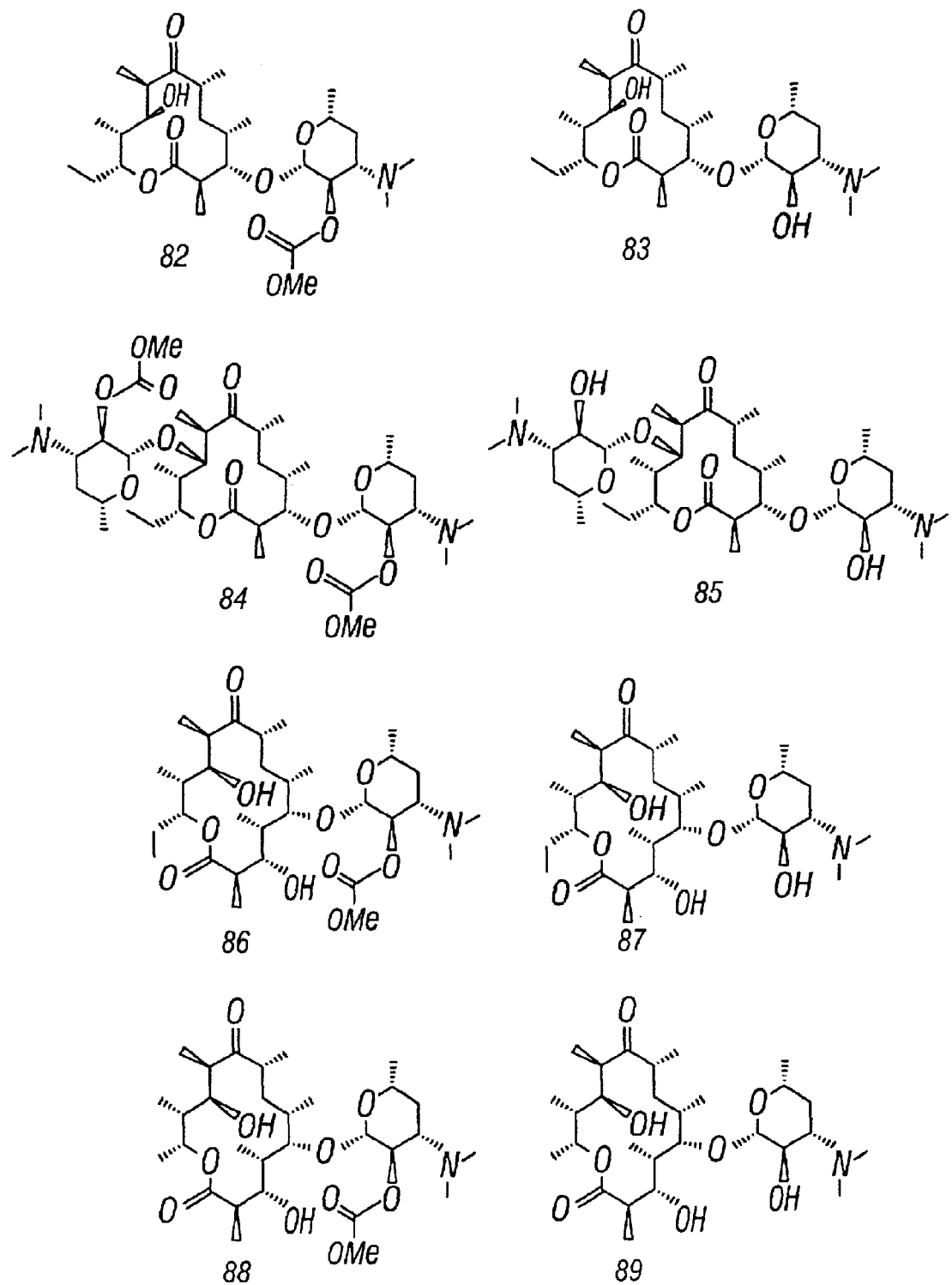
FIGS. 8A and 8B shows antibiotics obtained from selected polyketides shown in FIGS. 6A–6F.
Figure 8B:
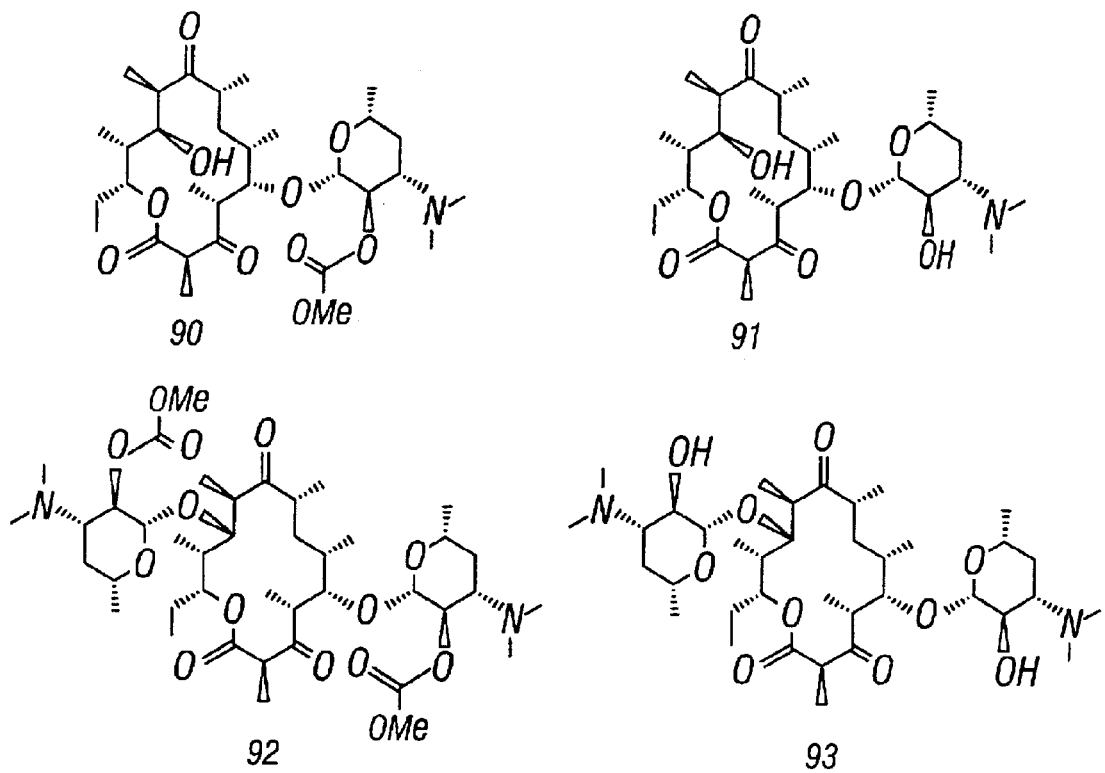

Particularly useful as antibiotics within the scope of the invention are compounds of formulas 82–93 as set forth in FIG. 8 herein.

Figure 9:
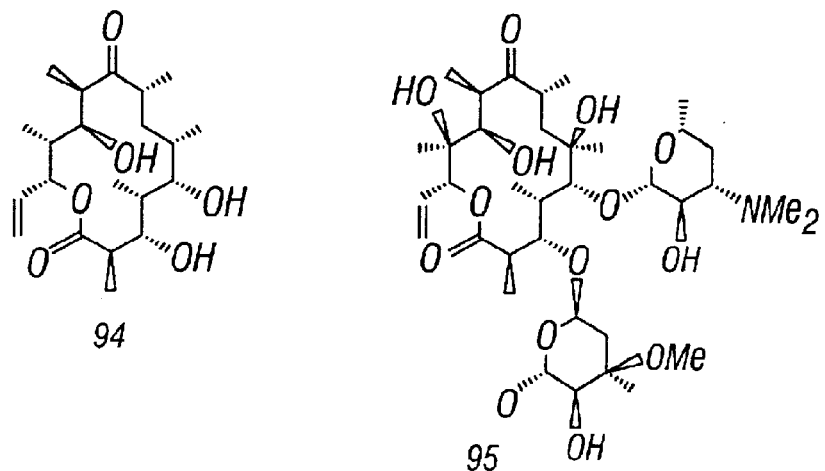
FIG. 9 shows a polyketide containing an unsaturated starter moiety and the corresponding antibiotic.

Still another embodiment of the compounds of the invention is set forth as compound 94 in FIG. 9. Its glycosylated form, shown as compound 95, is useful as an antibiotic.

EXAMPLES

The following examples are intended to illustrate, but not to limit the invention.

Materials and Methods

General Techniques

Bacterial strains, plasmids, and culture conditions. *S. coelicolor* CH999 described in WO 95/08548, published 30

Mar. 1995 was used as an expression host. DNA manipulations were performed in *Escherichia coli* MC1061. Plasmids were passaged through *E. coli* ET12567 (dam dcm hsdS Cm$^r$) (MacNeil, D. J. *J Bacteriol* (1988) 170:5607) to generate unmethylated DNA prior to transformation of *S. coelicolor*. *E. coli* strains were grown under standard conditions. *S. coelicolor* strains were grown on R2YE agar plates (Hopwood, D. A. et al. *Genetic manipulation of Streptomyces. A laboratory manual.* The John Innes Foundation: Norwich, 1985). pRM5, also described in WO 95/08548, includes a colEI replicon, an appropriately truncated SCP2* *Streptomyces* replicon, two act-promoters to allow for bidirectional cloning, the gene encoding the actII-ORF4 activator which induces transcription from act promoters during the transition from growth phase to stationary phase, and appropriate marker genes. Engineered restriction sites facilitate the combinatorial construction of PKS gene clusters starting from cassettes encoding individual domains of naturally occurring PKSs.

When pRM5 is used for expression of PKS, (i) all relevant biosynthetic genes are plasmid-borne and therefore amenable to facile manipulation and mutagenesis in *E. coli*, (ii) the entire library of PKS gene clusters can be expressed in the same bacterial host which is genetically and physiologically well-characterized and presumably contains most, if not all, ancillary activities required for in vivo production of polyketides, (iii) polyketides are produced in a secondary metabolite-like manner, thereby alleviating the toxic effects of synthesizing potentially bioactive compounds in vivo, and (iv) molecules thus produced undergo fewer side reactions than if the same pathways were expressed in wild-type organisms or blocked mutants.

Manipulation of DNA and organisms. Polymerase chain reaction (PCR) was performed using Taq polymerase (Perkin Elmer Cetus) under conditions recommended by the enzyme manufacturer. Standard in vitro techniques were used for DNA manipulations (Sambrook, et al. *Molecular Cloning: A Laboratory Manual* (Current Edition)). *E. coli* was transformed with a Bio-Rad *E. Coli* Pulsing apparatus using protocols provided by Bio-Rad. *S. coelicolor* was transformed by standard procedures (Hopwood, D. A. et al. *Genetic manipulation of Streptomyces. A laboratory manual.* The John Innes Foundation: Norwich, 1985) and transformants were selected using 2 mL of a 500 µg/ml thiostrepton overlay.

Preparation A

Construction of the Complete Erythromycin PKS Gene Cluster

Recovery of the Erythromycin PKS Genes

Although various portions of the erythromycin PKS gene cluster can be manipulated separately at any stage of the process of preparing libraries, it may be desirable to have a convenient source of the entire gene cluster in one place. Thus, the entire erythromycin PKS gene cluster can be recovered on a single plasmid if desired. This is illustrated below utilizing derivatives of the plasmid pMAK705 (Hamilton et al. *J Bacteriol* (1989) 171:4617) to permit in vivo recombination between a temperature-sensitive donor plasmid, which is capable of replication at a first, permissive temperature and incapable of replication at a second, non-permissive temperature, and recipient plasmid. The eryA genes thus cloned gave pCK7, a derivative of pRM5 (McDaniel et al. *Science* (1993) 262:1546). A control plasmid, pCK7f, was constructed to carry a frameshift mutation in eryAI. pCK7 and pCK7f possess a ColEI replicon for genetic manipulation in *E. coli* as well as a truncated SCP2* (low copy number) *Streptomyces* replicon.

These plasmids also contain the divergent actI/actIII promoter pair and actII-ORF4, an activator gene, which is required for transcription from these promoters and activates expression during the transition from growth to stationary phase in the vegetative mycelium. High-level expression of PKS genes occurs at the onset of the stationary phase of mycelial growth. The recombinant strains therefore produce the encoded polyketides as secondary metabolites.

Figure 3:
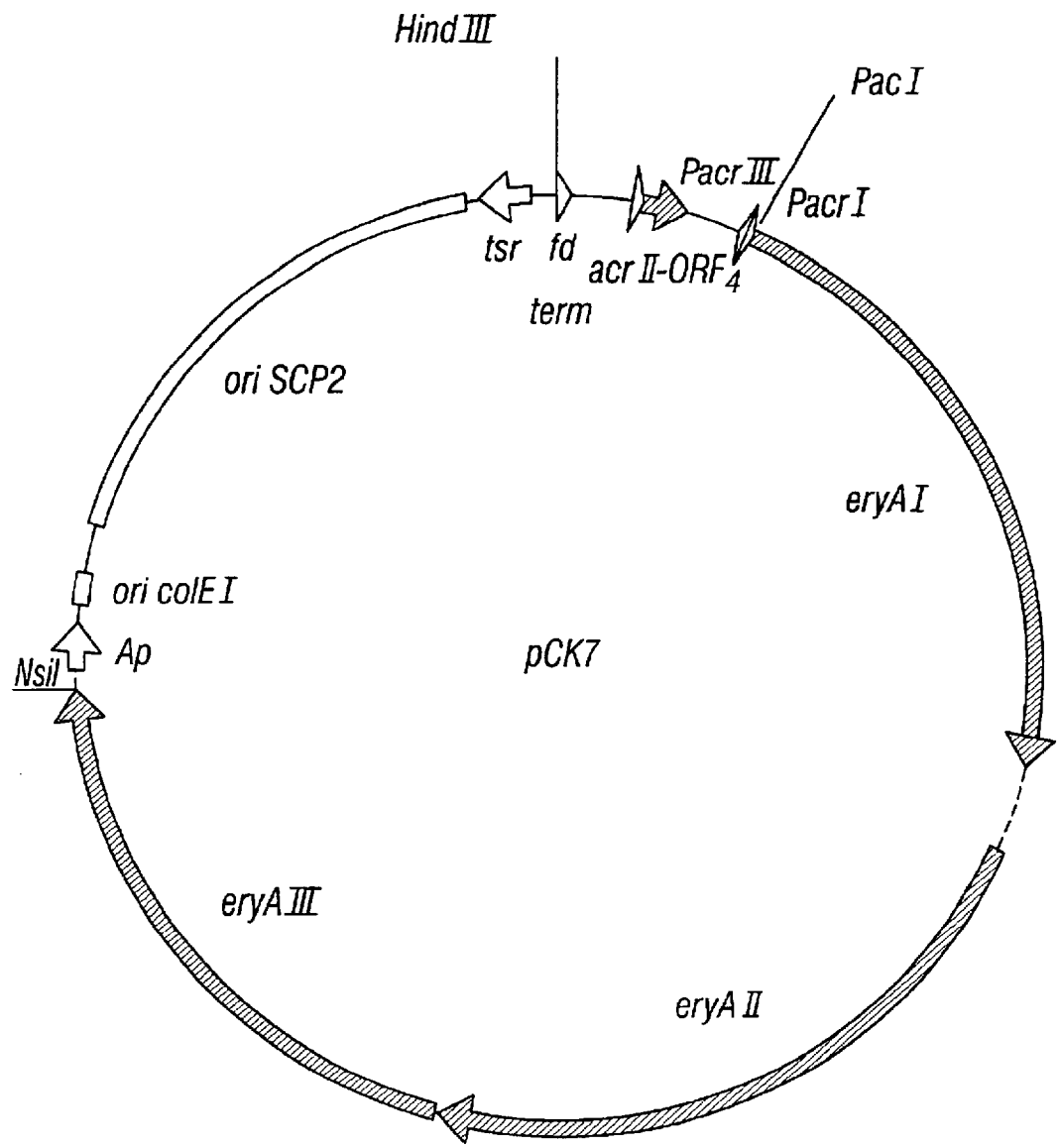
FIG. 3 shows a diagram of a vector containing the entire erythromycin gene cluster.
Figure 4:
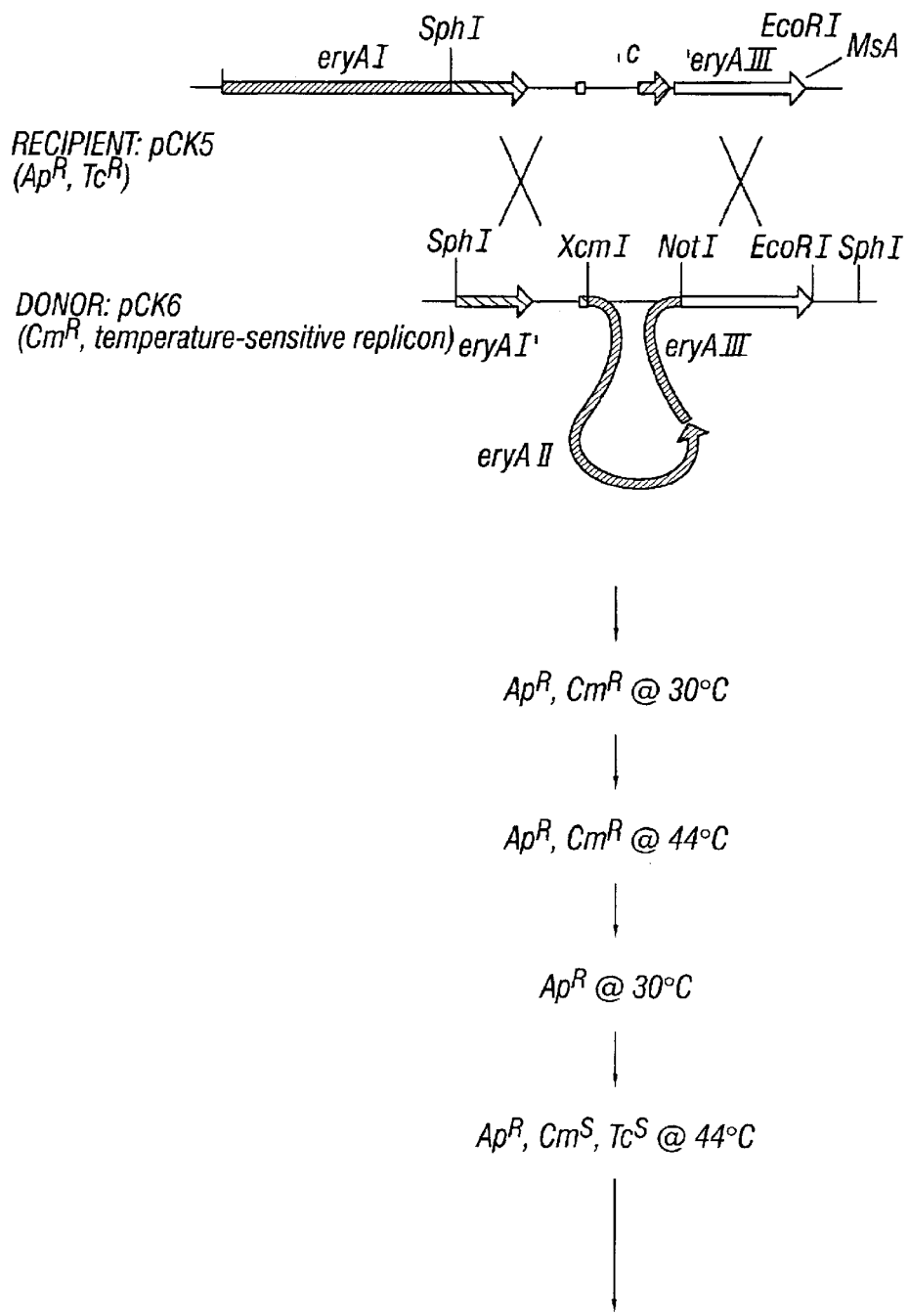
FIG. 4 shows a method for the construction of the vector of FIG. 3.

In more detail, pCK7 FIG. 3, a shuttle plasmid containing the complete eryA genes, which were originally cloned from pS1 (Tuan et al. *Gene* (1990) 90:21), was constructed as follows. The modular DEBS PKS genes were transferred incrementally from a temperature-sensitive "donor" plasmid, i.e., a plasmid capable of replication at a first, permissive temperature and incapable of replication at a second, non-permissive temperature, to a "recipient" shuttle vector via a double recombination event, as depicted in FIG. 4. A 25.6 kb SphI fragment from pS1 was inserted into the SphI site of pMAK705 (Hamilton et al. *J Bacteriol* (1989) 171:4617) to give pCK6 (Cm$^R$), a donor plasmid containing eryAII, eryAIII, and the 3' end of eryAI. Replication of this temperature-sensitive pSC101 derivative occurs at 30° C. but is arrested at 44° C. The recipient plasmid, pCK5 (Ap$^R$, Tc$^R$), includes a 12.2 kb eryA fragment from the eryAI start codon (Caffrey et al. *FEBS Lett* (1992) 304:225) to the XcmI site near the beginning of eryAII, a 1.4 kb EcoRI-BsmI pBR322 fragment encoding the tetracycline resistance gene (Tc), and a 4.0 kb NotI-EcoRI fragment from the end of eryAIII. PacI, NdeI, and ribosome binding sites were engineered at the eryAI start codon in pCK5. pCK5 is a derivative of pRM5 (described above). The 5' and 3' regions of homology are 4.1 kb and 4.0 kb, respectively. MC1061 *E. coli* was transformed with pCK5 and pCK6 and subjected to carbenicillin and chloramphenicol selection at 30° C. Colonies harboring bath plasmids (Ap$^R$, Cm$^R$) were then restreaked at 44° C. on carbenicillin and chloramphenicol plates. Only cointegrates formed by a single recombination event between the two plasmids were viable. Surviving colonies were propagated at 30° C. under carbenicillin selection, forcing the resolution of the cointegrates via a second recombination event. To enrich for pCK7 recombinants, colonies were restreaked again on carbenicillin plates at 44° C. Approximately 20% of the resulting colonies displayed the desired phenotype (Ap$^R$, Tc$^S$, Cm$^S$). The final pCK7 candidates were thoroughly checked via restriction mapping. A control plasmid, pCK7f, which contains a frameshift error in eryAI, was constructed in a similar manner. pCK7 and pCK7f were transformed into *E. coli* ET12567 (MacNeil *J Bacteriol* (1988) 170:5607) to generate unmethylated plasmid DNA and subsequently moved into *Streptomyces coelicolor* CH999.

Upon growth of CH999/pCK7 on R2YE medium, the organism produced abundant quantities of two polyketides. The addition of propionate (300 mg/L) to the growth medium resulted in approximately a two-fold increase in yield of polyketide product. Proton and $^{13}$C NMR spectroscopy, in conjunction with propionic-1-$^{13}$C acid feeding experiments, confirmed the major product as 6dEB (>40 mg/L) (FIG. 1A). The minor product was identified as 8,8a-deoxyoleandolide (>10 mg/L) (FIG. 1A), which apparently originates from an acetate starter unit instead of propionate in the 6dEB biosynthetic pathway. $^{13}C_2$ sodium acetate feeding experiments confirmed the incorporation of acetate into the minor product. Three high molecular weight proteins (>200 kDa), presumably DEBS1, DEBS2, and DEBS3 (Caffrey et al. *FEBS Lett* (1992) 304:225), were also observed in crude extracts of CH999/pCK7 via SDS-polyacrylamide gel electrophoresis. No polyketide products were observed from CH999/pCK7f The inventors hereby acknowledge support provided by the American Cancer Society (IRG-32–34).

Example 1

Preparation of Scaffolds for Replacing DEBS AT and KR Domains

Figure 5:
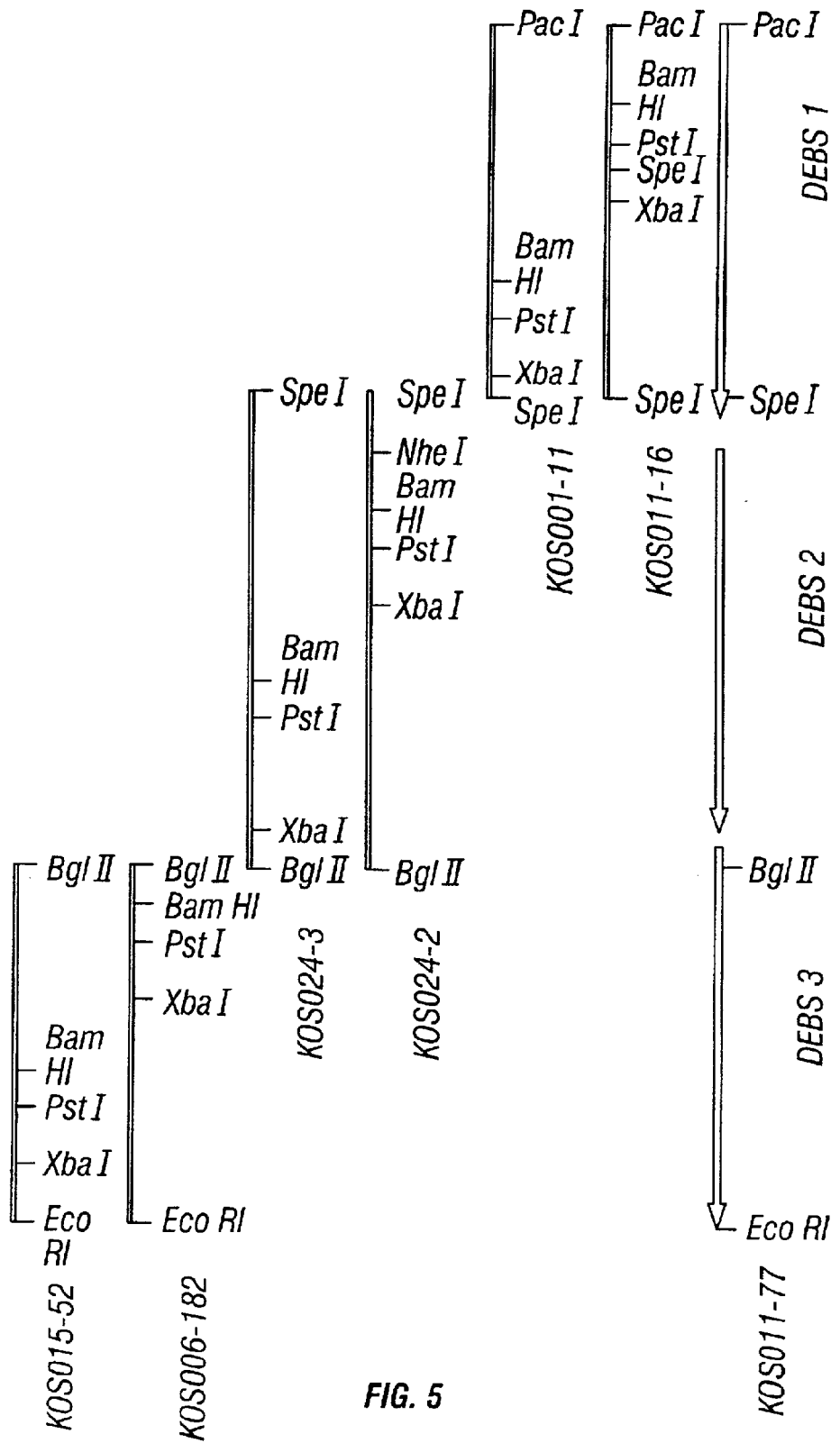
FIG. 5 shows a diagram of the erythromycin gene cluster with locations of restriction sites introduced for ease of manipulation.

For each of the six modules of DEBS, a subclone was made containing endonuclease restriction sites engineered at selected boundaries of the acyltransferase (AT) and reduction (KR or DH/ER/KR) domains. The restriction sites were introduced into the subclones by PCR mutagenesis. A BamHI site was used for the 5' boundary of AT domains, a PstI site was introduced between the AT and reductive domains, and XbaI was used at the 3' end of the reductive domain (see FIG. 5). This resulted in the following engineered sequences (lower case indicates engineered restriction site) (SEQ ID NOS:1–18, in order of appearance):

Module 1 (pKOS011-16)

| | |
|---|---|
| 5' AT boundary | GCGCAGCAG*ggatcc*GTCTTCGTC |
| AT/KR boundary | CGCGTCTGG*ctgcag*CCGAAGCCG |
| 3' KR boundary | CCGGCCGAA*tctaga*GTGGGCGCG |

Module 2 (pKOS001-11)

| | |
|---|---|
| 5' AT boundary | TCCGACGGT*ggatcc*GTGTTCGTC |
| AT/KR boundary | CGGTTCTGG*ctgcag*CCGGACCGC |
| 3' KR boundary | ACGGAGAGC*tctaga*GACCGGCTG |

Module 3 (pKOS024-2)

| | |
|---|---|
| 5' AT boundary | GACGGGCGC*ggatcc*GTCTTCCTG |
| AT/KR boundary | CGCTACTGG*ctgcag*CCCGCCGCA |
| 3' KR boundary | ACCGGCGAG*tctaga*CAACGGCTC |

Module 4 (pKOS024-3)

| | |
|---|---|
| 5' AT boundary | GCGCCGCGC*ggatcc*GTCCTGGTC |
| AT(DH/ER/KR) boundary | CGCTTCTGG*ctgcag*CCGCACCGG |
| 3' DH/ERJKR boundary | GGGCCGAAC*tctaga*GACCGGCTC |

Module 5 (pKOS006-182)

| | |
|---|---|
| 5' AT boundary | ACTCGCCGC*ggatcc*GCGATGGTG |
| AT/KR boundary | CGGTACTGG*ctgcag*ATCCCCACC |
| 3' KR boundary | GAGGAGGGC*tctaga*CTCGCCCAG |

Module 6 (pKOS015-52)

| | |
|---|---|
| 5' AT boundary | TCCGCCGGC*ggatcc*GTTTTCGTC |
| AT/KR boundary | CGGTACTGG*ctgcag*CCGGAGGTG |
| 3' KR boundary | GTGGGGCC*tctaga*GCGGTGCAG |

Example 2

Preparation of Cassettes from the Rapamycin PKS

A cosmid library of genomic DNA from *Streptomyces hygroscopicus* ATCC 29253 was used to prepare DNA cassettes prepared from the rapamycin PKS gene cluster to be used as replacements into the enzymatic activity regions of the erythromycin gene cluster. Cassettes were prepared by PCR amplification from appropriate cosmids or subclones using the primer pairs listed in Table 1, and were designed to introduce suitable restriction sites at the ends of the cassettes. The rapAT2 cassette is flanked by BglII and PstI sites, and the rapAT14 cassette is flanked by BamHI and PstI sites. The reductive cycle cassettes are flanked by PstI and XbaI sites. Large DH/ER/KR cassettes were amplified in two pieces, then joined at an engineered XhoI site in order to minimize errors introduced during PCR amplification of long DNA sequences. The rapKR4 cassette was made by cloning a 1.3 kb NheI/XbaI fragment from the rapDH/KR4 cassette above into the XbaI site in pUC19. There is a PstI site that is in-frame and upstream of XbaI in pUC 19 that generates the following junction at the 5'-end of the cassette:

5'-ctgcagGTCGAC<u>TCTAGC</u>CTGGT    (SEQ. ID. NO. 19)

TABLE 1

Primer pairs used for PCR amplification of rapamycin PKS cassettes. All primers are listed from 5' to 3'. Engineered restriction sites are lower case.

| Module | Primer Sequence (SEQ ID NOS:20–31) |
|---|---|
| rapAT2 | forward: TTT*agatct*GTGTTCGTCTTCCCGGGT |
| | Reverse: TTT*ctgcag*CCAGTACCGCTGGTGCTGGAAGGCGTA |
| rapAT14 | Forward: TTT*ggatcc*GCCTTCCTGTTCGACGGGCAAGGC |
| | Reverse: TTT*ctgcag*CCAGTAGGACTGGTGCTGGAACGG |
| rapKR2 | Forward: TTT*ctgcag*GAGGGCACGGACCGGGCGACTGCGGGT |
| | Reverse: TTT*tctaga*ACCGGCGGCAGCGGCCCGCCGAGCAAT |
| rapDH/KR4 | Forward: TTT*ctgcag*AGCGTGGACCGGGCGGCT |
| | Reverse: TTT*tctaga*GTCACCGGTAGAGGCGGCCCT |
| rapDH/ER/KR1 (left half) | Forward: TTT*ctgcag*GGCGTGGACCGGGCGGCTGCC |
| | Reverse: TTT*ctcgag*CACCACGCCCGCAGCCTCACC |
| rapDH/ER/KR1 (right half) | Forward: TTT*ctcgag*GTCGGTCCGGAGGTCCAGGAT |
| | Reverse: TTT*tctaga*ATCACCGGTAGAAGCAGCCCG |

Example 3

Replacement of DEBS Modules By Rapamycin PKS Cassettes

The following are typical procedures. The products are indicated by their numbers in FIG. 6, as well as listed in Table 2, below, where "a" represents the embodiment where R is methyl; "b" represents the embodiment where R is hydrogen.

a) Replacement of DEBS DH/ER/KR4. A portion of the erythromycin gene of module 4 (eryDH/ER/KR4) was replaced either with the corresponding rapamycin activities of the first rapamycin module (rapDH/ER/KR1) or of module 4 of rapamycin (rapDH/KR4). The replacement utilized the technique of Kao et al. *Science* (1994) 265:509–512. A donor plasmid was prepared by first amplifying 1 kbp regions flanking the DH/ER/KR4 of DEBS to contain a PstI site at the 3' end of the left flank and an XbaI site at the 5' end of the right flank. The fragments were ligated into a temperature-sensitive donor plasmid, in a manner analogous to that set forth for KR6 in paragraph b) of this example, and the rapamycin cassettes prepared as described in Example 2 were inserted into the PstI/XbaI sites. The recipient plasmid was pCK7 described in Preparation A. The in vivo recombination technique resulted in the expression plasmid pKOS011-19 (eryDH/ER/KR4→rapDH/ER/KR1) and pKOS011-21 (eryDH/ER/KR4→rapDH/KR4). The junctions at which the PstI and XbaI sites were introduced into DEBS in both vectors are as follows:

GAGCCCCAGCGGTACTGGCTGCAG rap cassette TCTA-GAGCGGTGCAGGCGGCCCCG (SEQ ID NOS:32–33)

The resulting expression vectors were transformed into *S. coelicolor* CH999 and successful transformants grown as described above. The transformant containing the rapDH/ER/KR1 cassette produced the polyketide shown in FIG. 6 as compound 23 and listed in Table 2 as 23a,b; the transformant containing the plasmid with rapDH/KR4 cassette produced the polyketide shown in FIG. 6 as compound 24 and listed in Table 2 as 24a,b. As shown, these polyketides differ from 6-deoxyerythronolide B by virtue of a 6,7 alkene in the case of 24a and by the C6-methyl stereochemistry in the case of 23a.

b) Replacement of DEBS KR6. In a manner analogous to that set forth in paragraph a), plasmid pKOS011-25, wherein eryKR6 was replaced by rapDH/KR4, was prepared by substituting regions flanking the KR6 domain of DEBS in construction of the donor plasmid.

Approximately 1 kb regions flanking the eryKR6 domain were PCR amplified with the following primers (SEQ ID NOS:34–37):

```
left flank
forward   5'-TTTGGATCCGTTTTCGTCTTCCCAGGTCAG reverse   5'-TTTCTGCAGCCAGTACCGCTGGGGCTCGAA right flank
forward   5'-TTTTCTAGAGCGGTGCAGGCGGCCCCGGCG reverse   5'-AAAATGCATCTATGAATTCCCTCCGCCCA
```

These fragments were then cloned into a pMAK705 derivative in which the multiple cloning site region was modified to accommodate the restriction sites of the fragments (i.e., BamHI/PstI for the left flank and XbaI/NsiI for the right flank). Cassettes were then inserted into the PstI/XbaI sites of the above plasmid to generate donor plasmids for the in vivo recombination protocol. The resulting PstI and XbaI junctions engineered into DEBS are as follows:

GAACACCAGCGCTTCTGGCTGCAG rap cassette TCTA-GAGACCGGCTCGCCGGTCGG (SEQ ID NOS:38–39)

Regions flanking the KR6 domain of DEBS were used to construct the donor plasmids.

Transformants of *S. coelicolor* CH999 resulted in the production of the polyketide shown in FIG. 6 as compound 74 and listed in Table 2 as 74a,b.

c) Replacement of DEBS KR2. The eryKR2 enzymatic activity was replaced in a series of vectors using in vitro insertion into the PstI/XbaI sites of pKAO263. pKAO263 is a derivative of pCK13 described in Kao, C. M. *J Am Chem Soc* (1996) 118:9184–9185. It was prepared by introducing the PstI and XbaI restriction sites positioned identically to those in the analogous 2-module DEBS system described by Bedford, D. et al. *Chem an Biol* (1996) 3:827–831. Three expression plasmids were prepared: pKOS009-7 (eryKR2→rapDH/KR4); pKAO392 (eryKR2→rapKR2); and pKAO410 (eryKR2→rapDH/ER/KR1). These plasmids, when transformed into *S. coelicolor* CH999, resulted in the production of polyketides with the structures 12a,b; 3a,b; and 10a, 11a,b listed in Table 2 and shown in FIG. 6, respectively. An additional vector, pKAO400 (eryKR2→rapKR4) produced the same results as pKAO392.

d) Replacement of DEBS AT2. The DEBS AT activity from module 2 was excised after inserting restriction sites BamHI and PstI flanking the AT module 2 domain into pCK12 (Kao et al. *J Am Chem Soc* (1995) 112:9105–9106). After digestion with BamHI/PstI, the BgII/PstI fragment containing rapAT2 was inserted. The resulting engineered DEBS/rapAT2 junction is as follows (BamHI/BglII ligation -GGATCT; PstI -CTGCAG):

```
AGTGCCTCCGACGGTGGATCT   rapAT2   CTGCAGCCGGACCGCACCACCCCT (SEQ ID NOS:40-41)
```

*S. coelicolor* CH999 transformed with the resulting plasmid, pKOS008-51, produced the polyketides 6a,b shown in FIG. 6 as structure 6.

Example 4

Excision of DEBS Reductive Cycle Domains

The following is a typical procedure. The products are indicated by their numbers in FIG. 6, and listed in Table 2, where "a" represents the embodiment where R is methyl; "b" represents the embodiment where R is hydrogen.

A duplex oligonucleotide linker (ΔRdx) was designed to allow complete excision of reductive cycle domains. Two synthetic oligonucleotides (SEQ ID NOS:42–43):

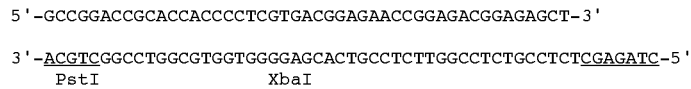

were designed to generate PstI- and XbaI-compatible ends upon hybridization. This duplex linker was ligated into the PstI- and XbaI-sites of the recombination donor plasmid containing the appropriate left- and right-flanking regions of the reductive domain to be excised. The in vivo recombination technique of Example 3, paragraph a) was then used. The donor plasmid contained the duplex linker ΔRdx having a PstI and XbaI compatible end ligated into the PstI and XbaI sites of the plasmid modified to contain the left and right flanking regions of the reductive domain to be excised. The donor plasmids were recombined with recipient plasmid pCK7 to generate pKOS011-13 (eryKR6→ΔRdx) and with recipient plasmid pCK13 to obtain pKOS005-4 (eryKR2→ΔRdx). When transformed into *S. coelicolor* CH999, plasmid pKOS011-13 produced the polyketides listed in Table 2 as 30a,b, 31a,b, 77a,b and 78a,b and shown in FIG. 6 as structures 30, 31, 77, and 78; and plasmid pKOS005-4 produced the polyketide listed in Table 2 as 2a,b, and shown in FIG. 6 as structure 2.

Example 5

Manipulation of Macrolide Ring Size by Directed Mutagenesis of DEBS

The following are typical procedures. The products are indicated by their numbers in FIG. 6 and listed in Table 2, where "a" represents the embodiment where R is methyl; "b" represents the embodiment where R is hydrogen.

Using the expression system of Kao, C. M. et al. *Science* (1994) 265:509–512, the expression of DEBS1 alone (1+2), in the absence of DEBS2 and DEBS3 (in plasmid pCK9), resulted in the production of (2R,3S,4S,5R)-2,4-dimethyl-3,5-dihydroxy-n-heptanoic acid L-lactone ("the heptanoic acid L-lactone" (see FIG. 6, compound 1, and FIG. 7A))(1–3 mg/L), the expected triketide product of the first two modules (Kao, C. M. et al. *J Am Chem Soc* (1994) 116:11612–11613). Thus, a thioesterase is not essential for release of a triketide from the enzyme complex.

Two additional deletion mutant PKS were constructed. The first contained DEBS1 fused to the TE, and the second PKS included the first five DEBS modules fused to the TE. Plasmids pCK12 and pCK15 respectively contained the genes encoding the bimodular ("1+2+TE") and pentamodular ("1+2+3+4+5+TE") PKSs.

The 1+2+TE PKS in pCK12 contained a fusion of the carboxy-terminal end of the acyl carrier protein of module 2 (ACP-2) to the carboxy-terminal end of the acyl carrier protein of module 6 (ACP-6). Thus ACP-2 is essentially intact and is followed by the amino acid sequence naturally found between ACP-6 and the TE. Plasmid pCK12 contained eryA DNA originating from pS1 (Tuan, J. S. et al. *Gene* (1990) 90:21). pCK12 is identical to pCK7 (Kao et al. *Science* (1994), supra) except for a deletion between the carboxy-terminal ends of ACP-2 and ACP-6. The fusion occurs between residues L3455 of DEBS1 and Q2891 of DEBS3. An SpeI site is present between these two residues so that the DNA sequence at the fusion is CTCACTAGT-CAG. (SEQ ID NO;44).

The 1+2+3+4+5+TE PKS in pCK15 contained a fusion 76 amino acids downstream of the β-ketoreductase of module 5 (KR-5) and five amino acids upstream of ACP-6. Thus, the fusion occurs towards the carboxy-terminal end of the non-conserved region between KR-5 and ACP-5, and the recombinant module 5 was essentially a hybrid between the wild type modules 5 and 6. Plasmid pCK15 contained eryA DNA originating from pS1 (Tuan et al. *Gene* (1990), supra). pCK15 is a derivative of pCK7 (Kao et al. *Science* (1994), supra) and was constructed using the in vivo recombination strategy described earlier (Kao et al *Science* (1994), supra). pCK 15 is identical to pCK7 with the exception of a deletion between KR-5 and ACP-6, which occurs between residues G1372 and A2802 of DEBS3, and the insertion of a blunted a SalI fragment containing a kanamycin resistance gene (Oka A. et al. *J Mol Biol* (1981) 147:217) into the blunted HindIII site of pCK7. An arginine residue is present between G1372 and A2802 so that the DNA sequence at the fusion is GGCCGCGCC.

Figures 7A, 7B:
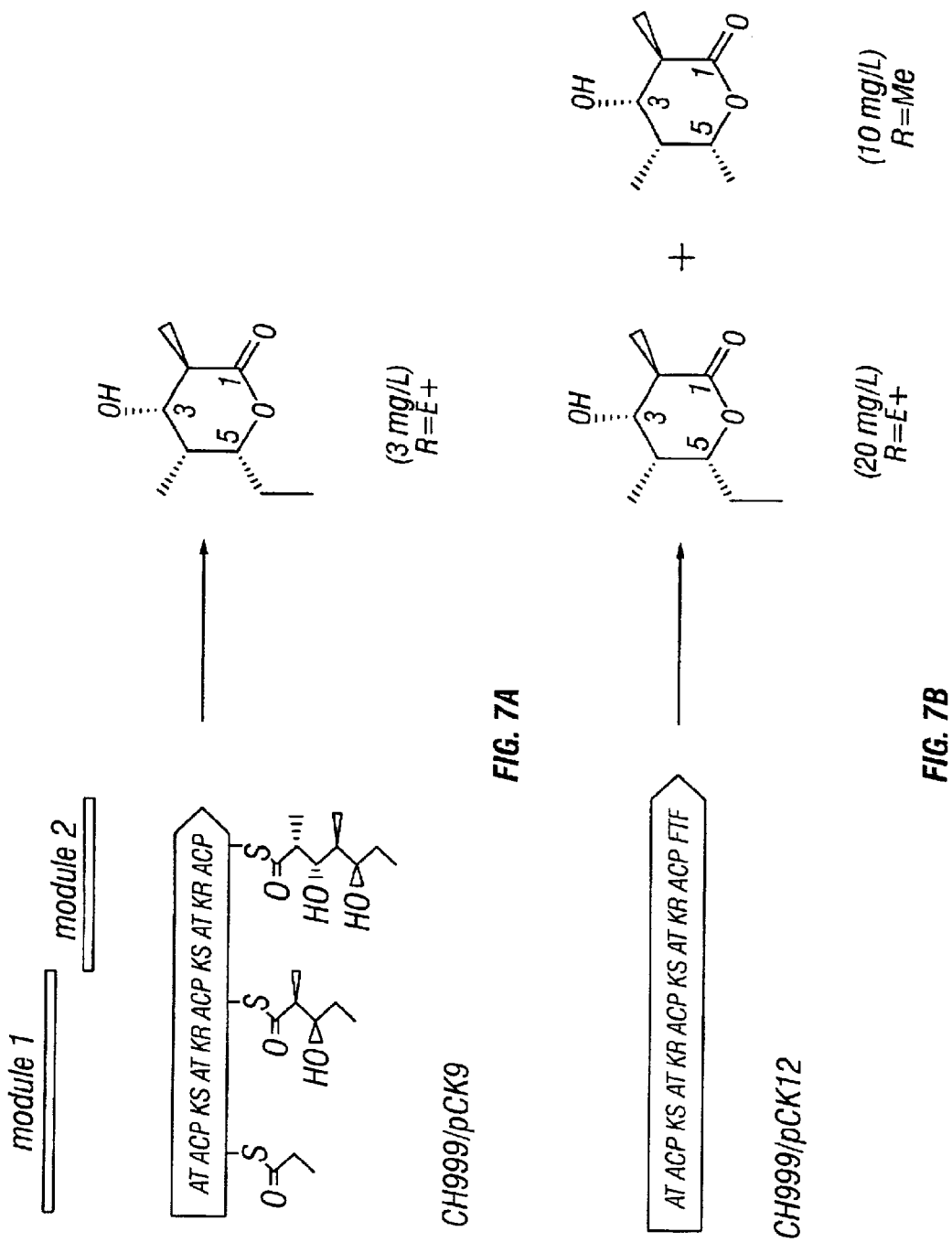
FIGS. 7A, 7B, and 7C show the construction of derivative PKS gene clusters from the vector of FIG. 3.
Figure 7C:
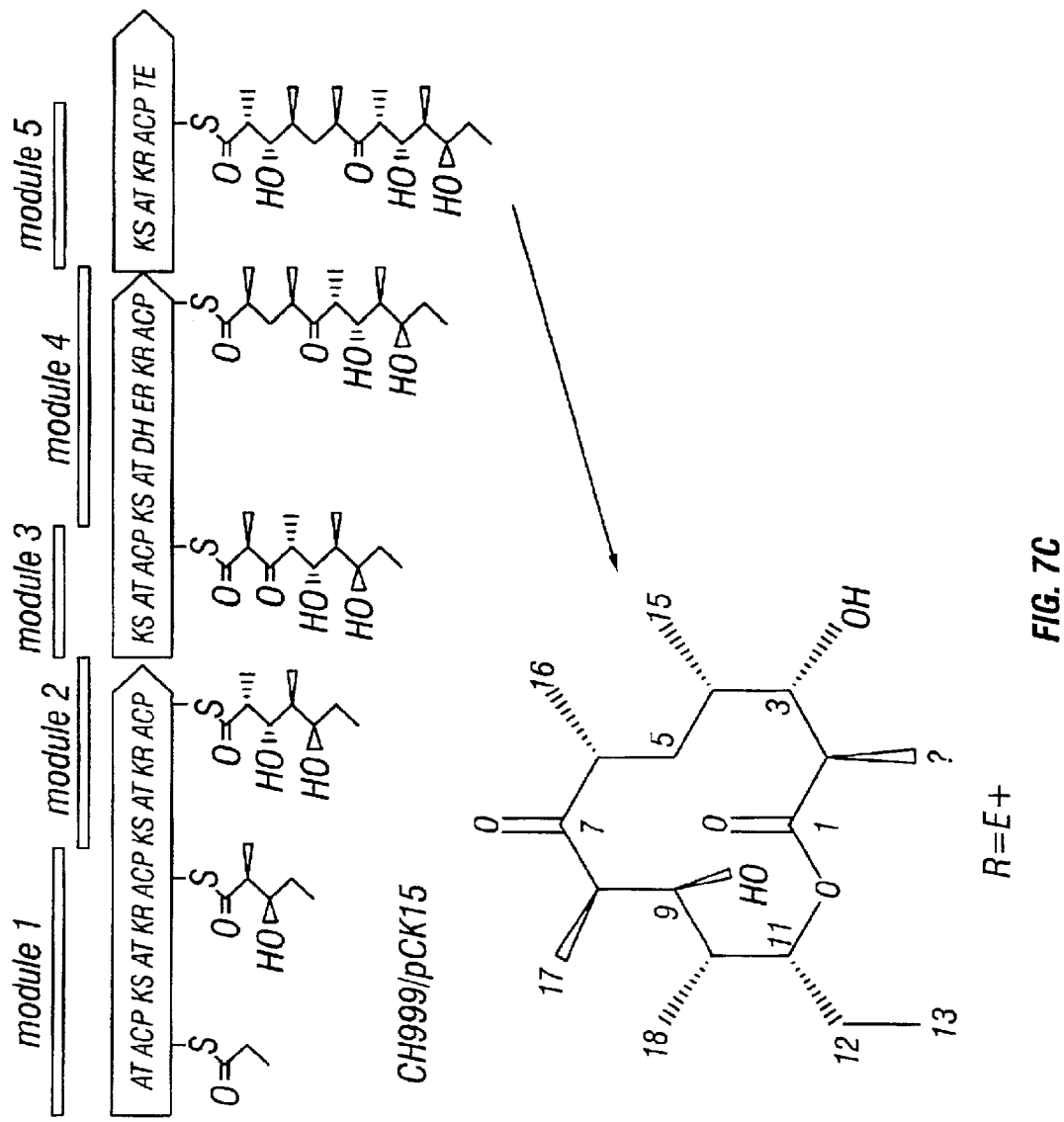

Plasmids pCK12 and pCK15 were introduced into *S. coelicolor* CH999 and polyketide products were purified from the transformed strains according to methods previously described (Kao et al. *Science* (1994), supra). The products obtained from various transformants: CH999/pCK12 and CH999/pCK15 as well as CH999/pCK9 described above, are shown in FIG. 7.

CH999/pCK12 produced the heptanoic acid L-lactone (1a) (20 mg/L) as determined by $^1$H and $^{13}$C NMR spectroscopy. This triketide product is identical to that produced by CH999/pCK9, which expresses the unmodified DEBS1 protein alone described above. However, CH999/pCK12 produced compound 1a (compound 1. where R is methyl. in FIG. 6) in significantly greater quantities than did CH999/pCK9 (>10 mg/L vs. ~1 mg/L), indicating the ability of the TE to catalyze thiolysis of a triketide chain attached to the ACP domain of module 2. CH999/pCK12 also produced significant quantities of compound 1b, a novel analog of compound 1a, (10 mg/L), that resulted from the incorporation of an acetate start unit instead of propionate. This is reminiscent of the ability of CH999/pCK7, which expresses the intact PKS, to produce 8,8a-deoxyoleandolide (see FIG. 1A) in addition to 6dEB described above.

Since compound 1b was not detected in CH999/pCK9, its facile isolation from CH999/pCK12 provides additional evidence for the increased turnover rate of DEBS1 due to the presence of the TE. In other words, the TE can effectively recognize an intermediate bound to a "foreign" module that is four acyl units shorter than its natural substrate, 6dEB. However, since the triketide products can probably cyclize spontaneously into compounds 1a and 1b under typical fermentation conditions (pH 7), it is not possible to discriminate between a biosynthetic model involving enzyme-catalyzed lactonization and one involving enzyme-catalyzed hydrolysis followed by spontaneous lactonization. Thus, the ability of the 1+2+TE PKS to recognize the C-5 hydroxyl of a triketide as an incoming nucleophile is unclear.

CH999/pCK15, produced abundant quantities of (8R,9S)-8,9-dihydro-8-methyl-9-hydroxy-10-deoxymethonolide (compound 13 in FIG. 6) (10 mg/L), demonstrating that the pentamodular PKS is active. Compound 13 was characterized using $^1$H and $^{13}$C NMR spectroscopy of natural abundance and $^{13}$C-enriched material, homonuclear correlation spectroscopy (COSY), heteronuclear correlation spectroscopy (HETCOR), mass spectrometry, and molecular modeling. Compound 13 is an analog of 10-deoxymethonolide (compound 14, Lambalot, R. H. et al. *J Antibiotics* (1992) 45:1981–1982), the aglycone of the macrolide antibiotic methymycin. The production of compound 13 by a pentamodular enzyme demonstrates that active site domains in modules 5 and 6 in DEBS can be joined without loss of activity. Thus, it appears that individual modules as well as active sites are independent entities which do not depend on association with neighboring modules to be functional. The 12-membered lactone ring, formed by esterification of the terminal carboxyl with the C-11 hydroxyl of the hexaketide product, indicated the ability of the 1+2+3+4+5+TE PKS, and possibly the TE itself, to catalyze lactonization of a polyketide chain one acyl unit shorter than the natural product of DEBS, 6dEB. Indeed, the formation of compound 13 may mimic the biosynthesis of the closely related 12-membered hexaketide macrolide, methymycin, which frequently occurs with the homologous 14-membered heptaketide macrolides, picromycin and/or narbomycin (Cane, D. E. et al. *J Am Chem Soc* (1993) 115:522–566). The erythromycin PKS scaffold can thus be used to generate a wide range of macrolactones with shorter as well as longer chain lengths.

The construction of the 1+2+3+4+5+TE PKS resulted in the biosynthesis of a previously uncharacterized 12-membered macrolactone that closely resembles, but is distinct from, the aglycone of a biologically active macrolide. The apparent structural and functional independence of active site domains and modules as well as relaxed lactonization specificity suggest the existence of many degrees of freedom for manipulating these enzymes to produce new modular PKSs.

Example 6

Production and Analysis of Polyketide Products

The expression vectors created by domain substitution in DEBS, as described in Examples 1–5, were transformed into either *Streptomyces coelicolor* CH999 or *S. lividans* K4–114 using standard techniques (D. A. Hopwood et al. (1985) "Genetic Manipulation of *Streptomyces*: A Laboratory Manual," (The John Innes Foundation, Norwich)). Both host strains have complete deletions of the native actinorhodin polyketide synthase gene cluster and so produce no native polyketide products. Transformants were grown on 150 mm R2YE agar plates for 2 days at 30° C., at which time the agar slab was lifted from the dish and placed in a new dish which contained a layer of 4 mm glass beads, 50 mL of liquid R2YE medium supplemented with 5 mM sodium propionate, and ca. 1 g of XAD-16 resin beads. This was kept at 30° C. for an additional 7 days.

The XAD-16 resin was collected by vacuum filtration, washed with water, then extracted twice with 10 mL portions of ethanol. The extracts were combined and evaporated to a slurry, which was extracted with ethyl acetate. The ethyl acetate was washed once with sat. $NaHCO_3$ and evaporated to yield the crude product. Samples were dissolved in ethanol and analyzed by LC/MS. The HPLC used a 4.6×150 mm C18 reversed-phase column with a gradient from 80:19:1 $H_2O/CH_3CN/CH_3CO_2H$ to 99:1 $CH_3CN/CH_3CO_2H$. Mass spectra were recorded using a Perkin-Elmer/Sciex API100LC spectrometer fitted with an APCI ion source. Each genetic construct typically resulted in formation of products in pairs, indicated in Table 2 by the letters "a" (R=CH3) and "b" (R=H), arising from priming of the PKS by and propionyl-CoA and acetyl-CoA, respectively.

Additional Examples

Using the foregoing techniques, the DEBS constructs shown in Table 2 were prepared. The products obtained when the constructs were transformed into *S. coelicolor* CH999 are indicated by their numbers in FIG. 6 and in Table 2, where "a" represents the embodiment where R is methyl; "b" represents the embodiment where R is hydrogen. Some of the expression vectors were prepared by in vitro ligation; multiple domain substitutions were created by subsequent an vitro ligations into the singly-substituted expression plasmids. Others were obtained by in vivo recombination.

TABLE 2

| Plasmid | Modules | Domain Substitution | Products (see FIG. 6) |
|---|---|---|---|
| In Vitro Ligation | | | |
| KOS011-28 | 2 | eryAT1 → rapAT2 | 4-nor-TKL (5a,b) |
| KOS008-51 | 2 | eryAT2 → rapAT2 | 2-nor-TKL (6a,b) |
| KOS014-62 | 2 | eryKR2 → rapDH/ER/KR1 | 3-deoxy-TKL (4a,b) |
| KAO410 | 3 | eryKR2 → rapDH/ER/KR1 | KAO410 (10a,b) 3-deoxy-hemiketal (11a,b) |
| KAO392 | 3 | eryKR2 → rapKR2 | 3-epi-TKL (3a,b) |
| KOS009-7 | 3 | eryKR2 → rapDH/KR4 | KOS009-7 (12a,b) |
| KOS015-30 | 6 | eryAT3 → rapAT2 | 8-nor-6dEB (18a,b) |
| KOS016-47 | 6 | eryAT5 → rapAT2 | 4-nor-6dEB (19a,b) |
| KOS026-18b | 6 | eryKR5 → rapDH/ER/KR1 | 5-deoxy-6dEB (26a,b) |
| KOS016-32 | 6 | eryKR5 → rapDH/KR4 | 4,5-anhydro-6dEB (27a,b) |
| KOS016-28 | 6 | eryKR5 → ΔRdx | 5-oxo-6dEB (28a,b) |
| KOS015-63 | 6 | eryAT6 → rapAT2 | 2-nor-6dEB (20a,b) |
| KOS015-83 | 6 | eryAT2 → rapAT2 + eryKR2 → rapDH/KR4 | 10-nor-10,11-anhydro-6dEB (32a,b) |
| KOS015-84 | 6 | eryAT2 → rapAT2 + eryKR2 → rapDH/ER/KR1 | 10-nor-11-deoxy-6dEB (33a,b) |
| KOS016-100 | 6 | eryAT5 → rapAT2 + eryKR5 → Δrdx | 4-nor-5-oxo-6dEB (38a,b) |
| KOS015-106 | 6 | eryAT6 → rapAT2 + eryKR6 → rapKR2 | 2-nor-3-epi-6dEB (42a,b) |
| KOS015-109 | 6 | eryAT6 → rapAT2 + eryKR6 → Δrdx | 2-nor-3-oxo-6dEB (31a,b) |
| KOS011-90 | 6 | eryAT2 → rapAT2 + eryKR5 → rapDH/KR4 | 4,5-anhydro-10-nor-6dEB (34a,b) |
| KOS011-84 | 6 | eryAT2 → rapAT2 + eryKR5 → Δrdx | 5-oxo-10-nor-6dEB (35a,b) |
| KOS011-82 | 6 | eryKR2 → rapDH/KR4 + eryAT5 → rapAT2 | 4-nor-10,11-anhydro-6dEB (39a,b) |
| KOS011-85 | 6 | eryKR2 → rapDH/KR4 + eryKR5 → Δrdx | 5-oxo-10,11-anhydro-6dEB (57a,b) |
| KOS011-87 | 6 | eryKR2 → rapDH/KR4 + eryAT5 → rapAT2 + eryKR5 → Δrdx | 4-nor-5-oxo-10,11-anhydro-6dEB (65a,b) |
| KOS011-83 | 6 | eryKR2 → rapDH/ER/KR1 + eryAT5 → rapAT2 | 4-nor-11-deoxy-6dEB (40a,b) |
| KOS011-91 | 6 | eryKR2 → rapDH/ER/KR1 + eryKR5 → rapDH/KR4 | 4,5-anhydro-11-deoxy-6dEB (55a,b) |
| KOS011-86 | 6 | eryKR2 → rapDH/ER/KR1 + eryKR5 → Δrdx | 5-oxo-11-deoxy-6dEB (56a,b) |
| KOS011-88 | 6 | eryKR2 → rapDH/ER/KR1 + eryAT5 → rapAT2 + eryKR5 → Δrdx | 4-nor-5-oxo-11-deoxy-6dEB (69a,b) |
| KOS015-40 | 6 | eryAT2 → rapAT2 + eryKR6 → rapDH/KR4 | 2,3-anhydro-10-nor-6dEB (76a,b) |

TABLE 2-continued

| Plasmid | Modules | Domain Substitution | Products (see FIG. 6) |
|---|---|---|---|
| KOS015-41 | 6 | eryAT2 → rapAT2 + eryKR6 → Δrdx | 3-oxo-10-nor-6dEB (36a,b) 10-nor-spiroketal (79a,b) |
| KOS015-44 | 6 | eryKR2 → rapDH/ER/KR1 + eryAT6 → rapAT2 | 2-nor-11-deoxy-6dEB (45a,b) |
| KOS015-45 | 6 | eryKR2 → rapDH/ER/KR1 + eryKR6 → RapDH/KR4 | 2,3-anhydro-11-deoxy-6dEB (75a,b) |
| KOS015-46 | 6 | eryKR2 → rapDH/ER/KR1 + eryKR6 → Δrdx | 3-oxo-11-deoxy-6dEB (53a,b) |
| KOS015-42 | 6 | eryKR2 → rapDH/KR4 + eryAT6 → rapAT2 | 2-nor-10,11-anhydro-6dEB (46a,b) |
| KOS015-43 | 6 | eryKR2 → rapDH/KR4 + eryKR6 → Δrdx | 3-oxo-10,11-anhydro-6dEB (54a,b) |
| KOS015-88 | 6 | eryKR2 → rapDH/KR4 + eryKR6 → rapKR2 | 3-epi-10,11-anhydro-6dEB (48a,b) |
| KOS015-89 | 6 | eryKR2 → rapDH/ER/KR1 + eryKR6 → rapKR2 | 3-epi-11-deoxy-6dEB (49a,b) |
| KOS015-87 | 6 | eryAT2 → rapAT2 + eryKR6 → rapKR2 | 3-oxo-10-nor-6dEB (36a,b) |
| KOS015-117 | 6 | eryAT2 → rapAT14 + eryAT6 → rapAT2 | 2,10-bisnor-6dEB (37a,b) |
| KOS015-120 | 6 | eryAT2 → rapAT14 + eryAT6 → rapAT2 + eryKR6 → Δrdx | 2,10-bisnor-3-oxo-6dEB (58a,b) 2,10-bisnor-spiroketal (80a,b) |
| KOS015-121 | 6 | eryKR2 → rapDH/KR4 + eryAT6 → rapAT2 + eryKR6 → rapKR2 | 2-nor-3-epi-10,11-anhydro-6dEB (62a,b) |
| KOS015-122 | 6 | eryKR2 → rapDH/KR4 + eryAT6 → rapAT2 + eryKR6 → Δrdx | 2-nor-3-oxo-10,11-anhydro-6dEB (63a,b) |
| KOS015-123 | 6 | eryKR2 → rapDH/ER/KR1 + eryAT6 → rapAT2 + eryKR6 → rapKR2 | 2-nor-3-epi-11-deoxy-6dEB (66a,b) |
| KOS015-125 | 6 | eryKR2 → rapDH/ER/KR1 + eryAT6 → rapAT2 + eryKR6 → Δrdx | 2-nor-3-oxo-11-deoxy-6dEB (67a,b) |
| KOS015-127 | 6 | eryAT2 → rapAT2 + eryKR2 → rapDH/KR4 + eryKR6 → rapKR2 | 3-epi-10-nor-10,11-anhydro-6dEB (64a,b) |
| KOS015-150 | 6 | eryAT2 → rapAT2 + eryKR2 → rapDH/KR4 + eryAT6 → rapAT2 | 2,10-bisnor-10,11-anhydro-6dEB (59a,b) |
| KOS015-158 | 6 | eryAT2 → rapAT2 + eryKR2 → rapDH/ER/KR1 + eryKR6 → Δrdx | 3-oxo-10-nor-11-deoxy-6dEB (68a,b) |
| KOS015-159 | 6 | eryAT2 → rapAT2 + eryKR2 → rapDH/ER/KR1 + eryAT6 → rapAT2 | 2,10-bisnor-11-deoxy-6dEB (60a,b) |
| KOS016-133K | 6 | eryKR5 → rapDH/KR4 + eryKR6 → Δrdx | 3-oxo-4,5-anhydro-6dEB (51a,b) 3,5-dioxo-6dEB (52a,b) |
| KOS016-150B | 6 | eryKR5 → Δrdx + eryKR6 → rapKR4 | 3-epi-5-oxo-6dEB (50a,b) |
| KOS016-183F | 6 | eryAT5 → rapAT2 + eryAT6 → rapAT2 | 2,4-bisnor-6dEB (41a,b) |
| KOS016-183G | 6 | eryAT5 → rapAT2 + eryAT6 → rapAT2 + eryKR6 → rapKR2 | 2,4-bisnor-3-epi-6dEB (61a,b) |
| KOS016-152E | 6 | eryKR5 → rapDH/KR4 + eryAT6 → rapAT2 | 2-nor-4,5-anhydro-6dEB (43a,b) |
| KOS016-152F | 6 | eryKR5 → rapDH/KR4 + eryAT6 → rapAT2 + eryKR6 → rapKR2 | 2-nor-3-epi-4,5-anhydro-6dEB (70a,b) |
| KOS016-152G | 6 | eryKR5 → rapDH/KR4 + eryAT6 → rapAT2 + eryKR6 → Δrdx | 2-nor-3-oxo-4,5-anhydro-6dEB (71a,b) hemiketal (81a,b) |
| KOS016-152K | 6 | eryKR5 → Δrdx + eryAT6 → rapAT2 | 2-nor-5-oxo-6dEB (44a,b) |
| KOS016-152I | 6 | eryKR5 → Δrdx + eryAT6 → rapAT2 + eryKR6 → rapKR2 | 2-nor-3-epi-5-oxo-6dEB (72a,b) |
| KOS015-34 | 6 | eryAT3 → rapAT2 + eryAT6 → rapAT2 | 2,8-bisnor-6dEB (47a,b) |
| KOS015-162 | 6 | eryKR3 → rapDH/ER/KR1 + eryKR5 → Δrdx + eryAT6 → rapAT2 | 2-nor-5-oxo-11-deoxy-6dEB (73a,b) |

In Vivo Ligation

| Plasmid | Modules | Domain Substitution | Products (see FIG. 6) |
|---|---|---|---|
| KOS005-4 | 3 | KR2 → ΔRdx | 3-keto-TKL (2a,b) |
| KOS011-62 | 6 | AT2 → rapAT2 | 10-nor-6dEB (17a,b) |
| KOS011-66 | 6 | KR2 → rapDH/ER/KR1 | 11-deoxy-6dEB (21a,b) |
| KOS011-64 | 6 | KR2 → rapDH/KR4 | 10,11-anhydro-6dEB (22a,b) |
| KOS011-19 | 6 | DH/ER/KR4 → rapDH/ER/KR1 | 6-epi-6dEB (23a,b) |
| KOS011-21 | 6 | DH/ER/KR4 → rapDH/KR4 | 6,7-anhydro-6dEB (24a,b) |
| KOS011-22 | 6 | DH/ER/KR4 → ΔRdx | 7-oxo-6dEB (25a,b) |
| KOS011-74 | 6 | KR6 → rapKR2 | 3-epi-6dEB (29a,b) |
| KOS011-25 | 6 | KR6 → rapDH/KR4 | 2,3-anhydro-6dEB (74a,b) |
| KOS011-13 | 6 | KR6 → ΔRdx | 3-oxo-6dEB (30a,b) 2-nor-3-oxo-6dEB (31a,b) spiroketal (77a,b) 2-nor-spiroketal (78a,b) |

Example 7

Preparation of 14,15-dehydro-6-deoxyerythronolide B (Compound 94 of FIG. 9)

A 3 day culture of S. coelicolor CH999/pJRJ2 grown on 3 100-mm R2YE agar plates was overlayed with a solution of 10 mg of (2S,3R)-3-hydroxy-2-methyl-4-pentenoic acid N-acetylcysteamine thioester dissolved in 2 mL of 9:1 water/DMSO and allowed to dry. The culture was incubated at 30° C. for an additional 4 days. The agar was chopped and extracted twice with an equal volume of ethyl acetate. The extracts were combined and evaporated. Purification by silica gel chromatography (1:1 ethyl acetate/hexanes) yielded 0.75 mg of 14,15-dehydro-6-deoxyerythronolide B, compound 94 in FIG. 9, APCI-MS gives [M+H]+=385.

Figure 6G:
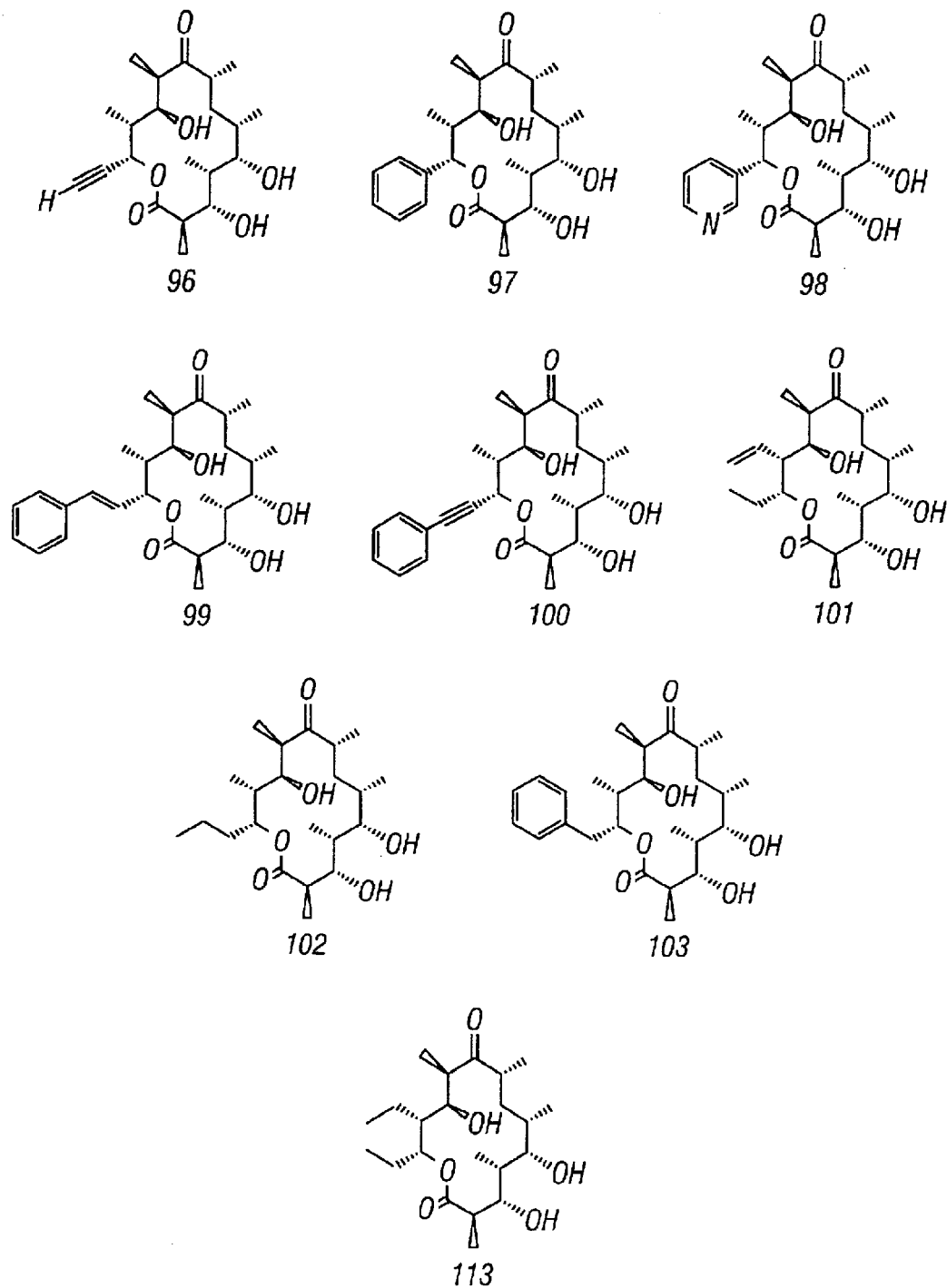
Figure 6H:
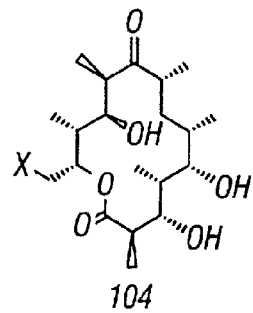
Figure 6H:
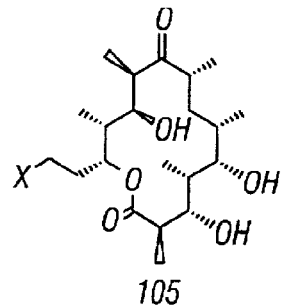
Figure 6H:
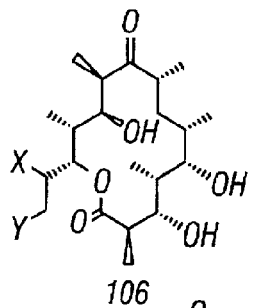
Figure 6H:
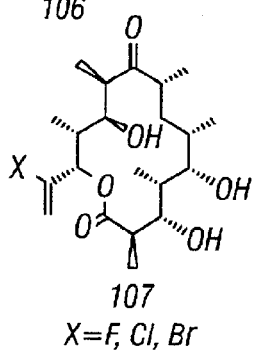
Figure 6H:
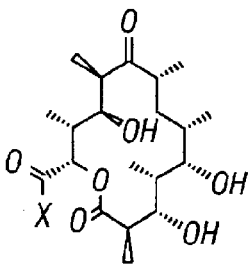
Figure 6H:
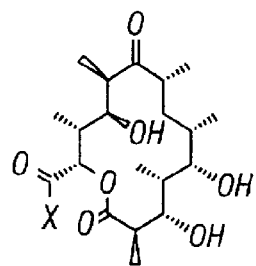
Figure 6H:
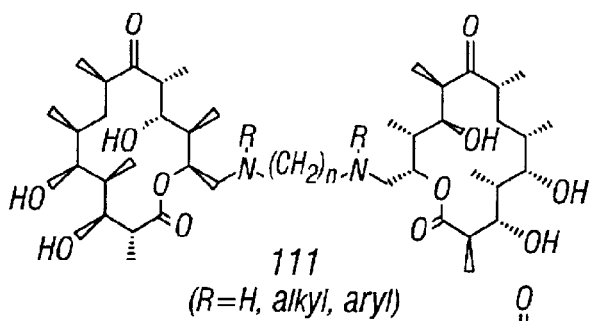
Figure 6H:
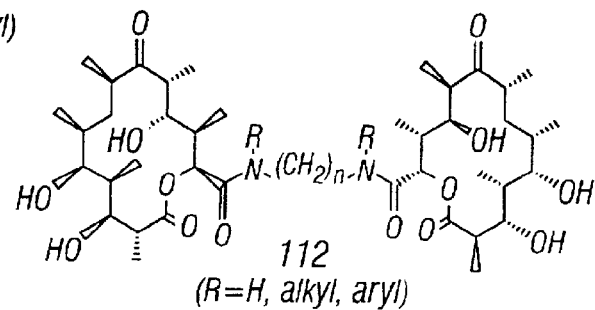

Analogous compounds with variations in R* and/or R¹ as represented by compounds 96–107 and compound 113 of FIGS. 6G and 6H are prepared in a similar manner as described in the previous paragraph but substituting the appropriate diketide as the N-acetylcysteamine thioester. These compounds are prepared in this manner and their structures verified.

The preparation of the appropriate derivatized diketides is described in Example 17.

Example 8

Synthesis of 1-(2-mercaptopyrimidinyl)-2-O-methoxycarbonyl-(D)-desosamine

Figure 10:
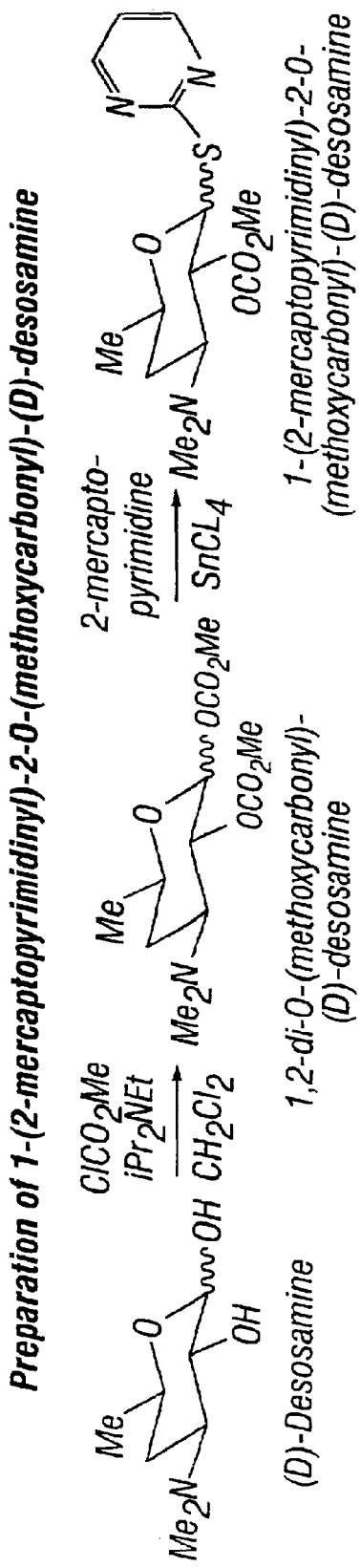
FIG. 10 shows the preparation of a reagent used to glycosylate polyketides to prepare the D-desosamine derivatives with antibiotic activity.

For the glycosylation reactions in the following examples, the title compound was used as a reagent. The conversions of paragraph (A) and (B) of this Example are shown in FIG. 10.

(A) Preparation of 1,2-di-O-methoxycarbonyl-(D)-desosamine: To 1.00 g of (D)-desosamine (4.74 mmol) in 50 mL $CH_2Cl_2$ was added 3.06 g of diisopropylethylamine. The mixture was stirred at ambient temperature for 10 min, then cooled to 4° C. Methyl chloroformate (1.34 g) was added dropwise at 4° C. The reaction mixture was allowed to warm to ambient temperature and stirred overnight. The solvent was evaporated to dryness, ethyl acetate (150 mL) was added to extract the product, and the remaining solid was filtered. The ethyl acetate was removed under vacuum and the crude product was purified on a silica gel column (ethyl acetate:methanol:triethylamine 84:5:1 v/v/v) to give 1.29 g of product (88% yield).

(B) Preparation of 1-(2-mercaptopyrimidinyl)-2-O-methoxycarbonyl-(D)-desosamine: A mixture of 1,2-di-O-methoxycarbonyl-(D)-desosamine (1.00 g, 3.436 mmol) and 0.7697 g of 2-mercaptopyrimdine (6.872 mmol) in a 25 mL 2-neck flash is dried under vacuum for 45 minutes. Dichloroethane (10 mL), toluene (5 mL), and DMF (5 mL) were added and stirred at ambient temperature followed by addition of 7 mL of $SnCl_4$ (1M in $CH_2Cl_2$). The reaction mixture was kept at 80° C. overnight. The reaction was terminated by addition of 1N NaOH until the mixture turned basic. The solution was extracted with 300 mL of ethyl acetate and the organic layer was washed with saturated aqueous $NaHCO_3$ (3×150 mL), dried over $Na_2SO_4$, filtered, and evaporated. The product was purified on a silica gel column (1:1 ethyl acetate:hexanes to ethyl acetate with 1% triethylamine) to obtain 0.25 g of 1-(2-mercaptopyrimidinyl)-2-O-methoxycarbonyl-(D)-desosamine and 0.5 g of recovered 1,2-di-O-methoxycarbonyl-(D)-desosamine.

Example 9

Preparation of 5-O-[1-β-(2-O-methoxycarbonyl-(D)-desosaminyl)]-6-deoxyerythronolide B and 5-O-(1-β-(D)-desosaminyl)-deoxyerythronolide B
(Compounds 86 and 87 in FIG. 8)

(A) mixture of 6-deoxyerythronolide B (6dEB) (15 mg, 39 umol) and 1-(2-mercaptopyrimidinyl)-2-O-methoxycarbonyl-(D)-desosamine (65 mg, 200 umol) was dried under vacuum, then placed under a nitrogen atmosphere. To this was added $CH_2Cl_2$ (1 mL), toluene (0.5 mL), and powdered 4A molecular sieves (50 mg), and the mixture was stirred for 10 minutes at ambient temperature. Silver trifluoromethanesulfonate (64 mg, 250 umol) was added and the reaction was stirred until LC/MS analysis indicated completion (18–20 hours). The mixture was filtered through anhydrous $Na_2SO_4$ and evaporated to yield crude product. The residue was dissolved in several drops of acetonitrile and loaded on a C-18 solid phase extraction cartridge (Whatman). Unreacted desosamine was removed by washing with 20% $CH_3CN/H_2O$ and glycosylation products and the remaining macrolide aglycone were recovered by eluting with 100% $CH_3CN$. Final separation was carried out by HPLC using a semiprep C-18 column (10 mm×150 mm) ($CH_3CN/H_2O$, 20% isocratic over 5 mm, then 20% to 80% over 30 mm). HPLC fractions were checked by LC/MS and fractions containing the same product were combined. The solvent was removed under vacuum, yielding 8.4 mg of 5-O-[1-β-(2-O-methoxycarbonyl-(D)-desosaminyl)]-6-deoxy-erythronolide B (compound 86 in FIG. 8) (36% yield). APCI-MS gives [M+H]+=602.

(B) 5-O-[1-(2-O-methoxycarbonyl-(D)-desosaminyl)]-6-deoxyerythronolide B (1–6 mg) from paragraph (A) was dissolved in 1 mL methanol, 0.2 mL H2O, and 0.2 mL triethylamine and kept at 70° C. for 3 hours. Removal of the solvent under vacuum gave crude product. This was dissolved in a few drops of $CH_3CN$ and applied to a Whatman C18 solid phase extraction cartridge. The column was washed with 25 mL of 20% $CH_3CN$ in water, then the product was eluted with 100% $CH_3CN$. Evaporation of the solvent gave 5-O-(1-β-(D)-desosaminyl)-6-deoxyerythronolide B (compound 87 in FIG. 8) in quantitative yield. APCI-MS gives [M+H]+=544.

Example 10

Preparation of 5-O-[1-β-(2-O-methoxycarbonyl-(D)-desosaminyl)]-8,8a-deoxyoleandolide and 5-O-(1-β-(D)-desosaminyl)]-8,8a-deoxyoleandolide (Compounds 88 and 89 in FIG. 8)

(A) Treatment of 8,8a-deoxyoleandolide (12 mg) as described in Example 9(A) yielded 5-O-[1-β-(2-O-methoxycarbonyl-(D)-desosaminyl)]-8,8a-deoxyoleandolide (60% yield) (compound 88 in FIG. 8). APCI-MS gives [M+H]+=508.

(B) Treatment of 5-O-[1-β-(2-methoxycarbonyl-(D)-desosaminyl)]-8,8a-deoxyoleandolide of paragraph (A) as described in Example 9(B) gave 5-O-(1-β-(D)-desosaminyl)-8,8a-deoxyoleandolide (compound 89 in FIG. 8) in quantitative yield. APCI-MS gives [M+H]+=530.

Example 11

Preparation of 5-O-[1-β-(2-methoxycarbonyl-(D)-desosaminyl)]-3,6-dideoxy-3-oxoerythronolide B (Compound 90 in FIG. 8) and 5,11-bis-(O-[1-β-(2-methoxycarbonyl-(D)-desosaminyl)])-3,6-dideoxy-3-oxoerythronolide B (Compound 92 in FIG. 8)

Treatment of 3,6-dideoxy-3-oxoerythronolide B (6 mg) as described in Example 9(A) gave 5-O-[1-β-(2-O-methoxycarbonyl-(D)-desosaminyl)]-3,6-dideoxy-3-oxoerythronolide B (compound 90 in FIG. 8) in 44% yield. APCI-MS gives [M+H]+=600. A second product, 5,11-bis-(O-[1-β-(2-O-methoxycarbonyl-(D)-desosaminyl)])-3,6-dideoxy-3-oxoerythronolide B (compound 92 in FIG. 8), was also isolated from this mixture in 26% yield; APCI-MS gives [M+H]+=815.

Example 12

Preparation of 5-O-(1-β-(D)-desosaminyl)-3,6-dideoxy-3-oxoerythronolide B (Compound 91 in FIG. 8) and of 5,11-bis-O-(1-β-(D)-desosaminyl)-3,6-dideoxy-3-oxoerythronolide B (Compound 93 in FIG. 8)

Treatment of 5-O-[1-β-(2-methoxycarbonyl-(D)-desosaminyl)]-3,6-dideoxy-3-oxoerythronolide B of Example 11 as described in Example 9(B) gave 5-O-(1-β-(D)-desosaminyl)-3,6-dideoxy-3-oxoerythronolide B (compound 91 in FIG. 8) in quantitative yield. APCI-MS gives [M+H]+=542.

Treatment of 5,11-bis-(O-[1-β-(2-methoxycarbonyl-(D)-desosaminyl)])-3,6-dideoxy-3-oxoerythronolide B of Example 11 as described in Example 9(B) gave 5,11-bis-O-(1-β-(D)-desosaminyl)-3,6-dideoxy-3-oxoerythronolide B (compound 93 in FIG. 8) in quantitative yield. APCI-MS gives [M+H]+=699.

Example 13

Preparation of 2'-O-methoxycarbonyl-(8R,9S)-10-deoxy-8,9-dihydro-9-hydroxy-8-methylmethymycin (Compound 83 in FIG. 8) and 3,9-bis-(O-[1-β-(2-methoxycarbonyl-(D)- desosaminyl)])-(8R,9S)-10-deoxy-8,9-dihydro-9-hydroxy-8-methylmethonolide (Compound 84 in FIG. 8)

Treatment of (8R,9S)-10-deoxy-8,9-dihydro-9-hydroxy-8-methylmethymycin (12 mg) according to the procedure of Example 9(A) yielded 2'-O-methoxycarbonyl-(8R,9S)-10-deoxy-8,9-dihydro-9-hydroxy-8-methylmethymycin (compound 82 in FIG. 8) (34%); APCI-MS gave [M+H]+=544. A second product, 3,9-bis-(O-[1-β-(2-O-methoxycarbonyl-(D)-desosaminyl)])-(8R,9S)-10-deoxy-8,9-dihydro-9-hydroxy-8-methylmethonolide (compound 84 in FIG. 8), was also isolated from this mixture (33%); APCI-MS gave [M+H]+=759.

Example 14

Preparation of (8,9S)-10-deoxy-8,9-dihydro-9-hydroxy-8-methylmethymycin (Compound 83 in FIG. 8) and of (8R,9S)-10-deoxy-8,9-dihydro-9-(1-β-(D)-desosaminyloxy)-8-methylmethymycin (Compound 85 in FIG. 8)

Treatment of 2'-O-methoxycarbonyl-(8R,9S)-10-deoxy-8,9-dihydro-9hydroxy-8-methylmethymycin of Example 13 as described in Example 9(B) gave (8R,9S)-10-deoxy-8,9-dihydro-9-hydroxy-8-methylmethymycin (compound 83 in FIG. 8) in quantitative yield. APCI-MS gives [M+H]+=486.

Treatment of 3,9-bis-(O-[1-β-(2-methoxycarbonyl-(D)-desosaminyl)])-(8R,9S)-10-deoxy-8,9-dihydro-9-hydroxy-8-methylmethonolide of Example 13 as described in Example 9(B) gave (8R,9S)-10-deoxy-8,9-dihydro-9-hydroxy-8-methylmethymycin (compound 85 in FIG. 8) in quantitative yield (elution from the C18 solid-phase extraction cartridge was with 100% methanol). APCI-MS gives [M+H]+=643.

Example 15

Preparation of 14,15-dehydroerythromycin A (Compound 95 in FIG. 9)

A sample of 14,15-dehydro-6-deoxyerythronolide B (0.75 mg) from Example 7 was dissolved in 0.6 mL of ethanol and diluted to 3 mL with sterile water. This solution was used to overlay a 3 day old culture of Saccharopolyspora erythraea WHM34 (eryA) grown on a 100 mm R2YE agar plate at 30° C. After drying, the plate was incubated at 30° C. for 4 days. The agar was chopped and extracted 3 times with 100 mL portions of 1% triethylamine in ethyl acetate. The extracts were combined and evaporated. The crude product was purified by preparative HPLC (C18 reversed phase, water-acetonitrile gradient containing 1% acetic acid). Fractions were analyzed by mass spectrometry, and those containing pure 14,15-dehydroerythromycin A (compound 95 in FIG. 9) were pooled, neutralized with triethylamine, and evaporated to a syrup. This was dissolved in water and extracted 3 times with equal volumes of ethyl acetate. The organic extracts were combined, washed once with saturated aqueous NaHCO$_3$, dried over Na$_2$SO$_4$, filtered, and evaporated to yield 0.15 mg of product. APCI-MS gives [M+H]+=733.

Example 16

Preparation of 14-oxo-8,8a-deoxyoleandolide (Compound 108) and 8,8a-deoxyoleandolide-14-carboxylic acid (Compound 109) and Derivatives Thereof These compounds can be prepared through ozonolysis of 14,15-dehydro-6-deoxyerythronolide B (compound 94 of FIG. 9).

A solution of compound 94 in methanol is cooled to −40° C., and ozone is bubbled into the solution until formation of I$_2$ is observed in a KI solution attached to the outlet of the reaction vessel. Excess ozone is purged from the solution by sparging with nitrogen gas, providing a solution of the ozonide of compound 94. Treatment of this solution with Me$_2$S will reduce the ozonide to the aldehyde, compound 108.

Alternatively, the ozonide can be oxidized by addition of H$_2$O$_2$ to provide the corresponding carboxylic acid, compound 109.

Methods for converting the aldehyde to amines via reductive amination (e.g., using an amine and NaBH$_3$CN under mildly acidic conditions, or through formation of an oxime followed by catalytic hydrogenation) are well known in the art. Similarly well known are methods for converting the carboxylic acid into esters or amides such as compound 110 (e.g., through activation using a carbodiimide reagent in the presence of an alcohol or an amine). Diamines in either procedure are used to produce dimeric macrolides such as compounds 111 and 112. (See FIG. 6H)

Example 17

Diketide thioester Synthesis: (2S,3R)-3-hydroxy-2-methyl-4-pentenoic acid N-acetylcysteamine thioester All diketide thioesters were synthesized by a common procedure. Illustrated here is the synthesis of (2S,3R)-3-hydroxy-2-methyl-4-pentenoic acid N-acetylcysteamine thioester. Enantioselective syn-aldol condensations were performed according to the procedure of D. A. Evans et al., *J Am Chem Soc* (1992) 114:9434–9453. Subsequent manipulations followed the general procedures of D. E. Cane et al., *J Antibiotics* (1995) 48: 647–651.

The synthesis of [4S,3(2S,3R)]-4-benzyl-3-(3-hydroxy-2-methyl-4-pentenoyl)-2-oxazolidinone by aldol condensation between (4S)-N-propionyl-4-benzyl-2-oxazolidinone (1.17 g, 5.0 mmol) and acrolein (0.4 mL, 11 mmol) was performed as described by D. A. Evans et al., *J Am Chem Soc* (1992) 114:9434–9453, yielding 0.72 g of the adduct (50% yield) after chromatography on SiO2(2:1 hexane/ethyl acetate).

The aldol adduct was treated with t-butyldimethylsilyl trifluoromethanesulfonate (0.63 mL, 2.7 mmol) and 2,6-lutidine (0.35 mL, 3 mmol) in THF at 0° C., yielding the O-silyl ether in quantitative yield after chromatography (4:1 hexane/ethyl acetate).

A solution of the O-silyl ether in 20 mL of THF was cooled on ice, and 2.8 mL of water was added followed by 0.61 mL of 50% H$_2$O$_2$. After 10 min, a solution of 215 mg of LiOH*H$_2$O in 2 mL of water was added. The reaction was monitored by TLC, which revealed completion after 1 hour. A solution of 1.25 g of sodium sulfite in 8 mL of water was added, and volatiles were removed by rotary evaporation under reduced pressure. The resulting aqueous mixture was extracted three times with 20 mL portions of CH$_2$Cl$_2$, then acidified to pH 2 using 6N HCl and extracted 3 times with 50 mL portions of ethyl acetate. The ethyl acetate extracts were combined, washed with brine, dried over Na$_2$SO$_4$, filtered, and evaporated to provide the product acid as a colorless oil, 470 mg (70%).

The acid was dissolved in 10 mL of anhydrous dimethylformamide and cooled on ice. After addition of diphenylphosphorylazide (1.25 mL) and triethylamine (1.06 mL), the mixture was stirred for 2 hrs on ice.

N-acetylcysteamine (1.5 mL) was added, and the mixture was stirred overnight at room temperature. After dilution with water, the mixture was extracted 3 times with ethyl acetate. The extracts were combined, washed with brine, dried over $Na_2SO_4$, filtered, and evaporated to provide the crude O-silyl thioester. Chromatography (1:1 hexane/ethyl acetate) provided pure product (460 mg, 70%).

The O-silyl thioester (400 mg) was dissolved in 25 mL of acetonitrile, and 5 mL of water was added followed by 2 mL of 48% HF. After 2 hours, an additional 2 mL of 48% HF was added. After a total of 3.5 hours, the reaction was stopped by addition of sat. $NaHCO_3$ to neutral pH. The product was extracted with 3 portions of ethyl acetate, and the combined extracts were washed with brine, dried over $Na_2SO_4$, filtered, and evaporated to provide the desilylated thioester. Chromatography (Ethyl acetate) gave 150 mg (56%) of pure (2S,3R)-3-hydroxy-2-methyl-4-pentenoic acid N-acetylcysteamine thioester, APCI-MC: [M+H]+= 232. 1H-NMR (CDCl3): d 5.83, 1H, ddd (J=5.6,10.8,17.5)-5.33, 1H, ddd (J=1.6,1.6,16.9); 5.22, 1H, ddd (J=1.5,1.5, 10.8); 4.45, 1H, m; 3.45, 2H, m; 3.04, 2H, m; 2.82, 1H, dq (J=4.3,6.8); 1.96, 3H, s; 1.22, 3H, d (J=6.8).

Other diketide thioesters were prepared by substitution of appropriate aldehydes in place of acrolein.

Example 18

Measurement of Antibacterial Activity

Antibacterial activity was determined using either disk diffusion assays with *Bacillus cereus* as the test organism or by measurement of minimum inhibitory concentrations (MIC) in liquid culture against sensitive and resistant strains of *Staphylococcus pneumoniae*.

What is claimed is:

1. The polyketide or glycosylated polyketide which has the formula:

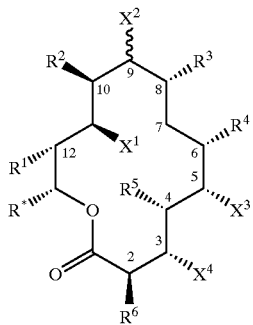

wherein R* is methyl or ethyl;
each of $R^1$–$R^6$ is methyl;
$X^1$ is OH or H; and/or
$X^2$ is =O, OH or H;
$X^3$ is OH or H;
$X^4$ is OH or H;
a pi bond is present at positions 10–11, 8–9, 4–5 and/or 2–3; and wherein at least one of the following characteristics is present:

$X^1$ is H;
$X^2$ is OH or H;
$X^3$ is H;
$X^4$ is H; or
a pi bond is present at positions 10–11, 8–9, 4–5 and/or 2–3.

2. The polyketide or glycosylated polyketide of claim 1 wherein at least 2 of said characteristics are present.

3. The polyketide or glycosylated polyketide of claim 2 wherein at least 3 of said characteristics are present.

4. The polyketide or glycosylated polyketide of claim 3 wherein at least 4 of said characteristics are present.

5. The polyketide or glycosylated polyketide of claim 1 wherein no more than 2 of said characteristics are present.

6. The polyketide or glycosylated polyketide of claim 1 wherein no more than 3 of said characteristics are present.

7. The polyketide or glycosylated polyketide of claim 1 wherein no more than 4 of said characteristics are present.

* * * * *

SEQUENCE LISTING

<160> NUMBER OF SEQ ID NOS: 44

<210> SEQ ID NO 1
<211> LENGTH: 24
<212> TYPE: DNA
<213> ORGANISM: Artificial Sequence
<220> FEATURE:
<223> OTHER INFORMATION: Module 1 - A BamHI site engineered for the 5'
      boundary of the acyltransferase domain.

<400> SEQUENCE: 1
gcgcagcagg gatccgtctt cgtc                                          24

<210> SEQ ID NO 2
<211> LENGTH: 24
<212> TYPE: DNA
<213> ORGANISM: Artificial Sequence
<220> FEATURE:
<223> OTHER INFORMATION: Module 1 - A PstI site engineered for
      introduction between the acyltransferase and reductive domains.

<400> SEQUENCE: 2
cgcgtctggc tgcagccgaa gccg                                          24

<210> SEQ ID NO 3
<211> LENGTH: 24
<212> TYPE: DNA
<213> ORGANISM: Artificial Sequence
<220> FEATURE:
<223> OTHER INFORMATION: Module 1 - A XbaI site engineered for
      introduction at the 3' end of the reductive domain.

<400> SEQUENCE: 3
gcgcgggtga gatctaagcc ggcc                                          24

<210> SEQ ID NO 4
<211> LENGTH: 24
<212> TYPE: DNA
<213> ORGANISM: Artificial Sequence
<220> FEATURE:
<223> OTHER INFORMATION: Module 2 - A BamHI site engineered for the 5'
      boundary of the acyltransferase domain.

<400> SEQUENCE: 4
tccgacggtg gatccgtgtt cgtc                                          24

<210> SEQ ID NO 5

```
<211> LENGTH: 24
<212> TYPE: DNA
<213> ORGANISM: Artificial Sequence
<220> FEATURE:
<223> OTHER INFORMATION: Module 2 - A PstI site engineered for
      introduction between the acyltransferase and reductive domains.

<400> SEQUENCE: 5
cggttctggc tgcagccgga ccgc                                        24

<210> SEQ ID NO 6
<211> LENGTH: 24
<212> TYPE: DNA
<213> ORGANISM: Artificial Sequence
<220> FEATURE:
<223> OTHER INFORMATION: Module 2 - A XbaI site engineered for
      introduction at the 3' end of the reductive domain.

<400> SEQUENCE: 6
gtcggccaga gatctcgaga ggca                                        24

<210> SEQ ID NO 7
<211> LENGTH: 24
<212> TYPE: DNA
<213> ORGANISM: Artificial Sequence
<220> FEATURE:
<223> OTHER INFORMATION: Module 3 - A BamHI site engineered for the 5'
      boundary of the acyltransferase domain.

<400> SEQUENCE: 7
gacgggcgcg gatccgtctt cctg                                        24

<210> SEQ ID NO 8
<211> LENGTH: 24
<212> TYPE: DNA
<213> ORGANISM: Artificial Sequence
<220> FEATURE:
<223> OTHER INFORMATION: Module 3 - A PstI site engineered for
      introduction between the acyltransferase and reductive domains.

<400> SEQUENCE: 8
cgctactggc tgcagcccgc cgca                                        24

<210> SEQ ID NO 9
<211> LENGTH: 24
<212> TYPE: DNA
<213> ORGANISM: Artificial Sequence
<220> FEATURE:
<223> OTHER INFORMATION: Module 3 - A XbaI site engineered for
      introduction at the 3' end of the reductive domain.

<400> SEQUENCE: 9
ctcggcaaca gatctgagcg gcca                                        24

<210> SEQ ID NO 10
<211> LENGTH: 24
<212> TYPE: DNA
<213> ORGANISM: Artificial Sequence
<220> FEATURE:
<223> OTHER INFORMATION: Module 4 - A BamHI site engineered for the 5'
      boundary of the acyltransferase domain.

<400> SEQUENCE: 10
gcgccgcgcg gatccgtcct ggtc                                        24

<210> SEQ ID NO 11
<211> LENGTH: 24
```

```
<212> TYPE: DNA
<213> ORGANISM: Artificial Sequence
<220> FEATURE:
<223> OTHER INFORMATION: Module 4 - A PstI site engineered for
      introduction between the acyltransferase and reductive domains.

<400> SEQUENCE: 11
cgcttctggc tgcagccgca ccgg                                              24

<210> SEQ ID NO 12
<211> LENGTH: 24
<212> TYPE: DNA
<213> ORGANISM: Artificial Sequence
<220> FEATURE:
<223> OTHER INFORMATION: Module 4 - A XbaI site engineered for
      introduction at the 3' end of the reductive domain.

<400> SEQUENCE: 12
ctcggccaga gatctcaagc cggg                                              24

<210> SEQ ID NO 13
<211> LENGTH: 24
<212> TYPE: DNA
<213> ORGANISM: Artificial Sequence
<220> FEATURE:
<223> OTHER INFORMATION: Module 5 - A BamHI site engineered for the 5'
      boundary of the acyltransferase domain.

<400> SEQUENCE: 13
actcgccgcg gatccgcgat ggtg                                              24

<210> SEQ ID NO 14
<211> LENGTH: 24
<212> TYPE: DNA
<213> ORGANISM: Artificial Sequence
<220> FEATURE:
<223> OTHER INFORMATION: Module 5 - A PstI site engineered for
      introduction between the acyltransferase and reductive domains.

<400> SEQUENCE: 14
cggtactggc tgcagatccc cacc                                              24

<210> SEQ ID NO 15
<211> LENGTH: 24
<212> TYPE: DNA
<213> ORGANISM: Artificial Sequence
<220> FEATURE:
<223> OTHER INFORMATION: Module 5 - A XbaI site engineered for
      introduction at the 3' end of the reductive domain.

<400> SEQUENCE: 15
gacccgctca gatctcggga ggag                                              24

<210> SEQ ID NO 16
<211> LENGTH: 24
<212> TYPE: DNA
<213> ORGANISM: Artificial Sequence
<220> FEATURE:
<223> OTHER INFORMATION: Module 6 - A BamHI site engineered for the 5'
      boundary of the acyltransferase domain.

<400> SEQUENCE: 16
tccgccggcg gatccgttttt cgtc                                             24

<210> SEQ ID NO 17
<211> LENGTH: 24
<212> TYPE: DNA
```

```
<213> ORGANISM: Artificial Sequence
<220> FEATURE:
<223> OTHER INFORMATION: Module 6 - A PstI site engineered for
      introduction between the acyltransferase and reductive domains.

<400> SEQUENCE: 17
cggtactggc tgcagccgga ggtg                                      24

<210> SEQ ID NO 18
<211> LENGTH: 24
<212> TYPE: DNA
<213> ORGANISM: Artificial Sequence
<220> FEATURE:
<223> OTHER INFORMATION: Module 6 - A XbaI site engineered for
      introduction at the 3' end of the reductive domain.

<400> SEQUENCE: 18
gacgtggcga gatctccggg ggtg                                      24

<210> SEQ ID NO 19
<211> LENGTH: 23
<212> TYPE: DNA
<213> ORGANISM: Artificial Sequence
<220> FEATURE:
<223> OTHER INFORMATION: A PstI site that is in-frame and upstream of
      XbaI in pUC19 that generates this junction at the 5'
      end of the cassette.

<400> SEQUENCE: 19
ctgcaggtcg actctagcct ggt                                       23

<210> SEQ ID NO 20
<211> LENGTH: 27
<212> TYPE: DNA
<213> ORGANISM: Artificial Sequence
<220> FEATURE:
<223> OTHER INFORMATION: Module rapAT2 (forward) Primer pairs used
      for PCR amplification of rapamycin PKS cassettes.

<400> SEQUENCE: 20
tttagatctg tgttcgtctt cccgggt                                   27

<210> SEQ ID NO 21
<211> LENGTH: 36
<212> TYPE: DNA
<213> ORGANISM: Artificial Sequence
<220> FEATURE:
<223> OTHER INFORMATION: Module rapAT2 (reverse) Primer pairs used for
      PCR amplification of rapamycin PKS cassettes.

<400> SEQUENCE: 21
tttctgcagc cagtaccgct ggtgctggaa ggcgta                         36

<210> SEQ ID NO 22
<211> LENGTH: 33
<212> TYPE: DNA
<213> ORGANISM: Artificial Sequence
<220> FEATURE:
<223> OTHER INFORMATION: Module rapAT14 (forward) Primer pairs used for
      PCR amplification of rapamycin PKS cassettes.

<400> SEQUENCE: 22
tttggatccg ccttcctgtt cgacgggcaa ggc                            33

<210> SEQ ID NO 23
<211> LENGTH: 33
<212> TYPE: DNA
```

```
<213> ORGANISM: Artificial Sequence
<220> FEATURE:
<223> OTHER INFORMATION: Module rapAT14 (reverse) Primer pairs used for
      PCR amplification of rapamycin PKS cassettes.

<400> SEQUENCE: 23
tttctgcagc cagtaggact ggtgctggaa cgg                                33

<210> SEQ ID NO 24
<211> LENGTH: 36
<212> TYPE: DNA
<213> ORGANISM: Artificial Sequence
<220> FEATURE:
<223> OTHER INFORMATION: Module rapKR2 (forward)  Primer pairs used for
      PCR amplification of rapamycin PKS cassettes.

<400> SEQUENCE: 24
tttctgcagg agggcacgga ccgggcgact gcgggt                             36

<210> SEQ ID NO 25
<211> LENGTH: 36
<212> TYPE: DNA
<213> ORGANISM: Artificial Sequence
<220> FEATURE:
<223> OTHER INFORMATION: Module rapKR2 (reverse)  Primer pairs used for
      PCR amplification of rapamycin PKS cassettes.

<400> SEQUENCE: 25
ttttctagaa ccggcggcag cggcccgccg agcaat                             36

<210> SEQ ID NO 26
<211> LENGTH: 26
<212> TYPE: DNA
<213> ORGANISM: Artificial Sequence
<220> FEATURE:
<223> OTHER INFORMATION: Module rapDH/KR4 (forward)  Primer pairs used
      for PCR amplification of rapamycin PKS cassettes.

<400> SEQUENCE: 26
ttctgcagag cgtggaccgg gcggct                                        26

<210> SEQ ID NO 27
<211> LENGTH: 30
<212> TYPE: DNA
<213> ORGANISM: Artificial Sequence
<220> FEATURE:
<223> OTHER INFORMATION: Module rapDH/KR4 (reverse)  Primer pairs used
      for PCR amplification of rapamycin PKS cassettes.

<400> SEQUENCE: 27
ttttctagag tcaccggtag aggcggccct                                    30

<210> SEQ ID NO 28
<211> LENGTH: 30
<212> TYPE: DNA
<213> ORGANISM: Artificial Sequence
<220> FEATURE:
<223> OTHER INFORMATION: Module rapDH/ER/KR1 (forward)  Primer pairs
      used for PCR amplification of rapamycin PKS cassettes.

<400> SEQUENCE: 28
tttctgcagg gcgtggaccg ggcggctgcc                                    30

<210> SEQ ID NO 29
<211> LENGTH: 30
<212> TYPE: DNA
<213> ORGANISM: Artificial Sequence
```

```
<220> FEATURE:
<223> OTHER INFORMATION: Module rapDH/ER/KR1 (reverse)  Primer pairs
      used for PCR amplification of rapamycin PKS cassettes.

<400> SEQUENCE: 29
tttctcgagc accacgcccg cagcctcacc                                    30

<210> SEQ ID NO 30
<211> LENGTH: 30
<212> TYPE: DNA
<213> ORGANISM: Artificial Sequence
<220> FEATURE:
<223> OTHER INFORMATION: Module rapDH/ER/KR1 (forward)  Primer pairs
      used for PCR amplification of rapamycin PKS cassettes.

<400> SEQUENCE: 30
tttctcgagg tcggtccgga ggtccaggat                                    30

<210> SEQ ID NO 31
<211> LENGTH: 30
<212> TYPE: DNA
<213> ORGANISM: Artificial Sequence
<220> FEATURE:
<223> OTHER INFORMATION: Module rapDH/ER/KR1 (reverse)  Primer pairs
      used for PCR amplification of rapamycin PKS cassettes.

<400> SEQUENCE: 31
ttttctagaa tcaccggtag aagcagcccg                                    30

<210> SEQ ID NO 32
<211> LENGTH: 24
<212> TYPE: DNA
<213> ORGANISM: Artificial Sequence
<220> FEATURE:
<223> OTHER INFORMATION: The junctions at which the PstI and XbaI sites
      were introduced into DEBS.

<400> SEQUENCE: 32
gagccccagc ggtactggct gcag                                          24

<210> SEQ ID NO 33
<211> LENGTH: 24
<212> TYPE: DNA
<213> ORGANISM: Artificial Sequence
<220> FEATURE:
<223> OTHER INFORMATION: The junctions at which the PstI and XbaI sites
      were introduced into DEBS.

<400> SEQUENCE: 33
tctagagcgg tgcaggcggc cccg                                          24

<210> SEQ ID NO 34
<211> LENGTH: 30
<212> TYPE: DNA
<213> ORGANISM: Artificial Sequence
<220> FEATURE:
<223> OTHER INFORMATION: A primer at which the eryKR6 domain was PCR
      amplified.

<400> SEQUENCE: 34
tttggatccg ttttcgtctt cccaggtcag                                    30

<210> SEQ ID NO 35
<211> LENGTH: 30
<212> TYPE: DNA
<213> ORGANISM: Artificial Sequence
<220> FEATURE:
```

```
<223> OTHER INFORMATION: A primer at which the eryKR6 domain was PCR
      amplified.

<400> SEQUENCE: 35 ttttctgcagc cagtaccgct ggggctcgaa                                     30

<210> SEQ ID NO 36
<211> LENGTH: 30
<212> TYPE: DNA
<213> ORGANISM: Artificial Sequence
<220> FEATURE:
<223> OTHER INFORMATION: A primer at which the eryKR6 domain was PCR
      amplified.

<400> SEQUENCE: 36
ttttctagag cggtgcaggc ggccccggcg                                      30

<210> SEQ ID NO 37
<211> LENGTH: 29
<212> TYPE: DNA
<213> ORGANISM: Artificial Sequence
<220> FEATURE:
<223> OTHER INFORMATION: A primer at which the eryKR6 domain was PCR
      amplified.

<400> SEQUENCE: 37
aaaatgcatc tatgaattcc ctccgccca                                       29

<210> SEQ ID NO 38
<211> LENGTH: 24
<212> TYPE: DNA
<213> ORGANISM: Artificial Sequence
<220> FEATURE:
<223> OTHER INFORMATION: The resulting PstI and XbaI junctions
      engineered into DEBS.

<400> SEQUENCE: 38
gaacaccagc gcttctggct gcag                                            24

<210> SEQ ID NO 39
<211> LENGTH: 24
<212> TYPE: DNA
<213> ORGANISM: Artificial Sequence
<220> FEATURE:
<223> OTHER INFORMATION: The resulting PstI and XbaI junctions
      engineered into DEBS.

<400> SEQUENCE: 39
tctagagacc ggctcgccgg tcgg                                            24

<210> SEQ ID NO 40
<211> LENGTH: 21
<212> TYPE: DNA
<213> ORGANISM: Artificial Sequence
<220> FEATURE:
<223> OTHER INFORMATION: Resulting engineered DEBS/rapAT2 junction.

<400> SEQUENCE: 40
agtgcctccg acggtggatc t                                               21

<210> SEQ ID NO 41
<211> LENGTH: 24
<212> TYPE: DNA
<213> ORGANISM: Artificial Sequence
<220> FEATURE:
<223> OTHER INFORMATION: Resulting engineered DEBS/rapAT2 junction.
```

```
<400> SEQUENCE: 41
ctgcagccgg accgcaccac ccct                                                24

<210> SEQ ID NO 42
<211> LENGTH: 47
<212> TYPE: DNA
<213> ORGANISM: Artificial Sequence
<220> FEATURE:
<223> OTHER INFORMATION: A synthetic oligonucleotide linker designed to
      allow complete excision of reductive cycle domains
      - designed to generate PstI- and XbaI-compatible
      ends upon hybridization.

<400> SEQUENCE: 42
gccggaccgc accacccctc gtgacggaga accggagacg gagagct                       47

<210> SEQ ID NO 43
<211> LENGTH: 55
<212> TYPE: DNA
<213> ORGANISM: Artificial Sequence
<220> FEATURE:
<223> OTHER INFORMATION: A synthetic oligonucleotide linker designed to
      allow complete excision of reductive cycle domains
      - designed to generate PstI- and XbaI-compatible
      ends upon hybridization.

<400> SEQUENCE: 43
ctagagctct ccgtctccgg ttctccgtca cgaggggtgg tgcggtccgg ctgca              55

<210> SEQ ID NO 44
<211> LENGTH: 12
<212> TYPE: DNA
<213> ORGANISM: Artificial Sequence
<220> FEATURE:
<223> OTHER INFORMATION: The fusion between the two residues L3455 of
      DEBS1 and Q2891 of DEBS3.

<400> SEQUENCE: 44
ctcactagtc ag                                                             12
```